(12) United States Patent
Kehler et al.

(10) Patent No.: US 8,552,045 B2
(45) Date of Patent: Oct. 8, 2013

(54) TRICYCLIC IMIDAZOLE COMPOUNDS AS PDE10 INHIBITORS

(75) Inventors: Jan Kehler, Lyngby (DK); Jacob Nielsen, København V (DK); Mauro Marigo, Skovlunde (DK); John Paul Kilburn, Haslev (DK); Morten Langgård, Glostrup (DK)

(73) Assignee: H. Lundbeck A/S, Valby (DK)

( * ) Notice: Subject to any disclaimer, the term of this patent is extended or adjusted under 35 U.S.C. 154(b) by 18 days.

(21) Appl. No.: 13/299,368

(22) Filed: Nov. 18, 2011

(65) Prior Publication Data

US 2012/0129836 A1 May 24, 2012

Related U.S. Application Data

(60) Provisional application No. 61/415,356, filed on Nov. 19, 2010.

(51) Int. Cl.
*A61K 31/415* (2006.01)

(52) U.S. Cl.
USPC .................. 514/393; 544/350; 546/119

(58) Field of Classification Search
USPC .......... 514/393; 544/350; 546/119; 548/302.4
See application file for complete search history.

(56) References Cited

FOREIGN PATENT DOCUMENTS

| WO | 2009/152825 A1 | 12/2009 |
| WO | 2010/145668 A1 | 12/2010 |
| WO | 2011/072694 A1 | 6/2011 |
| WO | 2011/072695 A1 | 6/2011 |
| WO | PCT/DK2011/000136 | 5/2012 |

*Primary Examiner* — Douglas M Willis
(74) *Attorney, Agent, or Firm* — Mary Catherine Di Nunzio; Kitae T. Lim

(57) ABSTRACT

This invention is directed to compounds with the structure

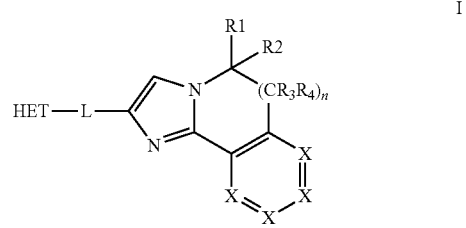

which are PDE10A enzyme inhibitors. The invention provides a pharmaceutical composition comprising a therapeutically effective amount of a compound of the invention and a pharmaceutically acceptable carrier. The present invention also provides processes for the preparation of the compounds of formula 1. The present invention further provides a method of treating a subject suffering from a neurodegenerative disorder comprising administering to the subject a therapeutically effective amount of a compound of formula 1. The present invention also provides a method of treating a subject suffering from a drug addiction comprising administering to the subject a therapeutically effective amount of a compound of formula 1. The present invention further provides a method of treating a subject suffering from a psychiatric disorder comprising administering to the subject a therapeutically effective amount of a compound of formula 1.

15 Claims, No Drawings

US 8,552,045 B2

TRICYCLIC IMIDAZOLE COMPOUNDS AS PDE10 INHIBITORS

FIELD OF THE INVENTION

The present invention provides compounds that are PDE10A enzyme inhibitors, and as such are useful to treat neurodegenerative and psychiatric disorders. Especially, the invention provides compounds that are highly selective for PDE10A enzyme over other PDE subtypes. The present invention also provides pharmaceutical compositions comprising compounds of the invention and methods of treating disorders using the compounds of the invention.

BACKGROUND OF THE INVENTION

Throughout this application, various publications are referenced in full. The disclosures of these publications are hereby incorporated by reference into this application to describe more fully the state of the art to which this invention pertains.

The cyclic nucleotides cyclic-adenosine monophosphate (cAMP) and cyclic-guanosine monophosphate (cGMP) function as intracellular second messengers regulating a vast array of processes in neurons. Intracellular cAMP and cGMP are generated by adenyl and guanyl cyclases, and are degraded by cyclic nucleotide phosphodiesterases (PDEs) via hydrolysis of the cyclic nucleotides into their respective nucleotide monophosphates.

Phosphodieasterase 10A (PDE10A) is a dual-specificity phosphodiesterase that can convert both cAMP to AMP and cGMP to GMP (Soderling, S. et al. *Proc. Natl. Acad. Sci.* 1999, 96, 7071-7076). PDE10A is primarily expressed in the neurons in the striatum, n. accumbens and in the olfactory tubercle (Kotera, J. et al. *Biochem. Biophys. Res. Comm.* 1999, 261, 551-557 and Seeger, T. F. et al. *Brain Research,* 2003, 985, 113-126).

Studies indicate that within the brain, PDE10 expression is expressed at high levels by the medium spiny neurons (MSN) of the caudate nucleus, the accumbens nucleus and the corresponding neurons of the olfactory tubercle. MSN express two functional classes of neurons: the $D_1$ class expressing $D_1$ dopamine receptors and the $D_2$ class expressing $D_2$ dopamine receptors. The $D_1$ class of neurons is part of the 'direct' striatal output pathway, which broadly functions to facilitate behavioral responses. The $D_2$ class of neurons is part of the 'indirect' striatal output pathway, which functions to suppress behavioral responses that compete with those being facilitated by the 'direct' pathway.

Dopamine $D_2$ receptor antagonism is well established in the treatment of schizophrenia. Since the 1950's, dopamine $D_2$ receptor antagonism has been the mainstay in psychosis treatment and all effective antipsychotic drugs antagonise $D_2$ receptors. The effects of $D_2$ are likely to be mediated primarily through neurons in the striatum, nucleus accumbens and olfactory tubercle, since these areas receive the densest dopaminergic projections and have the strongest expression of $D_2$ receptors (Konradi, C. and Heckers, S. *Society of Biological Psychiatry,* 2001, 50, 729-742).

Because PDE10A, in this context, has the desired expression profile with high and relatively specific expression in neurons in striatum, nucleus accumbens and olfactory tubercle, PDE10A inhibition is likely to have effects similar to $D_2$ receptor antagonism and therefore have antipsychotic effects.

While PDE10A inhibition is expected to mimic $D_2$ receptor antagonism in part, it might be expected to have a different profile. The $D_2$ receptor has signaling components besides cAMP (Neve, K. A. et al. *Journal of Receptors and Signal Transduction* 2004, 24, 165-205), wherefore interference with cAMP through PDE10A inhibition may reduce the risk of the extrapyramidal side effects that are seen with strong $D_2$ antagonism. Conversely, PDE10A inhibition may have some effects not seen with $D_2$ receptor antagonism. PDE10A is also expressed in $D_1$ receptors expressing striatal neurons (Seeger, T. F. et al. *Brain Research,* 2003, 985, 113-126).

Further, since $D_1$ receptor agonism leads to stimulation of adenylate cyclase and resulting increase in cAMP levels, PDE10A inhibition is likely to also have effects that mimic $D_1$ receptor agonism.

Finally, PDE10A inhibition will not only increase cAMP in cells, but might also be expected to increase cGMP levels, since PDE10A is a dual specificity phosphodiesterase. cGMP activates a number of target protein in cells like cAMP and also interacts with the cAMP signaling pathways.

In conclusion, PDE10A inhibition is likely to mimic $D_2$ receptor antagonism in part and therefore has antipsychotic effect, but the profile might differ from that observed with classical $D_2$ receptor antagonists.

The PDE10A inhibitor papaverine is shown to be active in several antipsychotic models. Papaverine potentiated the cataleptic effect of the $D_2$ receptor antagonist haloperidol in rats, but did not cause catalepsy on its own (WO 03/093499). Papaverine reduced hyperactivity in rats induced by PCP, while reduction of amphetamine induced hyperactivity was insignificant (WO 03/093499). These models suggest that PDE10A inhibition has the classic antipsychotic potential that would be expected from the theoretical considerations outlined above. WO 03/093499 further discloses the use of selective PDE10 inhibitors for the treatment of associated neurologic and psychiatric disorders. Furthermore, PDE10A inhibition reverses subchronic PCP-induced deficits in attentional set-shifting in rats (Rodefer et al. *Eur. J. Neurosci.* 2005, 4, 1070-1076). This model suggests that PDE10A inhibition might alleviate cognitive deficits associated with schizophrenia.

The tissue distribution of PDE10A indicates that PDE10A inhibitors can be used to raise levels of cAMP and/or cGMP within cells that express the PDE10A enzyme, especially neurons that comprise the basal ganglia, and the PDE10A inhibitors of the present invention would therefore be useful in treating a variety of associated neuropsychiatric conditions involving the basal ganglia such as neurological and psychiatric disorders, schizophrenia, bipolar disorder, psychosis and obsessive compulsive disorder, and may have the benefit of not possessing unwanted side effects, which are associated with the current therapies on the market.

Furthermore, recent publications (WO 2005/120514, WO 2005012485, Cantin et al, Bioorganic & Medicinal Chemistry Letters 17 (2007) 2869-2873) suggest that PDE10A inhibitors may be useful for treatment of obesity and non-insulin dependent diabetes.

Furthermore, recent publications suggest that PDE10A inhibitors may be useful for the treatment of Huntingtons Disease (Giampa et al. PLoS One 2010, 5(10), Giampa et al. Neurobiology of Disease (2009), 34(3), 450-456, Hebb et al. Current Opinion in Pharmacology 2007, 7(1), 86-92.)

With respect to inhibitors of PDE10A, EP 1250923 discloses the use of selective PDE10 inhibitors in general, and papaverine in particular, for the treatment of certain neurologic and psychiatric disorders.

Pyrrolodihydroisoquinolines and variants thereof are disclosed as inhibitors of PDE10 in WO 05/03129 and WO 05/02579. Piperidinyl-substituted quinazolines and isoquinolines that serve as PDE10 inhibitors are disclosed in WO 05/82883. WO 06/11040 discloses substituted quinazoline and isoquinoline compounds that serve as inhibitors of PDE10. US 20050182079 discloses substituted tetrahydroisoquinolinyl derivatives of quinazoline and isoquinoline that serve as effective phosphodiesterase (PDE) inhibitors. In particular, US 20050182079 relates to said compounds, which are selective inhibitors of PDE10. Analogously, US 20060019975 discloses piperidine derivatives of quinazoline and isoquinoline that serve as effective phosphodiesterase (PDE) inhibitors. US 20060019975 also relates to compounds that are selective inhibitors of PDE10. WO 06/028957 discloses cinnoline derivatives as inhibitors of PDE10 for the treatment of psychiatric and neurological syndromes. WO09/152,825 discloses phenylimidazole derivatives as compounds that serve as inhibitors of PDE10.

However, these disclosures do not pertain to the compounds of the invention, which are structurally unrelated to any of the known PDE10 inhibitors (Kehler, J. et al. *Expert Opin. Ther. Patents* 2007, 17, 147-158), and which have now been found by the inventors to be highly active and selective PDE10A enzyme inhibitors.

The present invention provides compounds that are PDE10A enzyme inhibitors and thus useful for treatment for neurodegenerative and/or psychiatric disorders, which are not efficacious in all patients. Hence, there remains a need for alternative methods of treatment.

SUMMARY OF THE INVENTION

The objective of the present invention is to provide compounds that are selective PDE10A enzyme inhibitors.

Another objective of the invention is to provide an effective treatment, in particular long-term treatment, of a human patient, without causing the side effects typically associated with current therapies for neurological and psychiatric disorders.

Further objectives of the invention will become apparent upon reading the present specification.

Accordingly, in one aspect the present invention relates to compounds of formula I

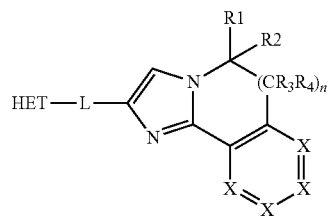

wherein
n is 0 or 1
X is selected from the group consisting of CH, CF, COCH3, COH, and N; with the limitation that no more than one X is N;
R1 and R2 are each selected independently from the group consisting of H; C1-C6 alkyl such as methyl, ethyl, 1-propyl, 2-propyl, isobutyl; C1-C6 alkyl(C3-C8)cycloalkyl such as cyclopropylmethyl; C1-C6 hydroxyalkyl such as hydroxyethyl; C1-C6 alkoxy such as methoxy and ethoxy; CH2CN; CH2C(O)NH2; C1-C6 arylalkyl such as benzyl and 4-chlorobenzyl; and C1-C6alkyl-heterocycloalkyl such as tetrahydropyran-4-yl-methyl and 2-morpholin-4-yl-ethyl; halogen such as F; and hydroxy;
R3 and R4 are each selected independently from the group consisting of H, OH, F, CH3, and OCH3.

Further, L is a linker selected from the group consisting of —CH=CH—, —CH$_2$—S—, —CH$_2$—CH$_2$— and —S—CH$_2$—; and HET is a heteroaromatic group of formula II containing from 2 to 4 nitrogen atoms:

wherein
Y can be N or CH, Z can be N or C; and
HET optionally can be substituted with up to three substituents R5, R6 and R7 individually selected from the group consisting of H; C1-C6 alkyl such as methyl; halogen such as chlorine, flour or bromine; cyano; halo(C1-C6)alkyl such as trifluoromethyl; aryl such as phenyl; alkoxy, preferably C1-C6 alkoxy, such as methoxy, dimethoxy, ethoxy, methoxy-ethoxy and ethoxy-methoxy, and C1-C6 hydroxyalkyl such as CH2CH2OH; and
"*" denotes the attachment point.

In a preferred embodiment of the invention R1 and R2 are independently selected from the group consisting of H, OH, F, CH3, and OCH3.

In another preferred embodiment of the invention R5, R6 and R7 are independently selected from the group consisting of H, CH3, and OCH3.

In another preferred embodiment R1 and R2 are independently selected from the group consisting of H, OH, F, CH3, and OCH3 while at the same time R5, R6 and R7 are independently selected from the group consisting of H, CH3, and OCH3.

Further, the invention relates to tautomers and pharmaceutically acceptable acid addition salts of a compound of formula I or II, and polymorphic forms thereof.

In a particular embodiment, the invention relates to a compound of formula I in the form of a single tautomer or a polymorph.

In separate embodiments of the invention, the compound of formula I is selected among the specific compounds disclosed in the examples of this application.

The invention further provides a compound of formula I, or a pharmaceutically acceptable acid addition salt thereof, for use as a medicament.

In another aspect, the present invention provides a pharmaceutical composition comprising a therapeutically effective amount of a compound of formula I and a pharmaceutically acceptable carrier, diluent or excipient.

The invention further provides the use of a compound of formula I, or a pharmaceutically acceptable acid addition salt thereof, for the preparation of a medicament for the treatment of a neurodegenerative or psychiatric disorder.

Furthermore, in yet another aspect, the present invention provides a method of treating a subject suffering from a neurodegenerative disorder, comprising administering to the subject a therapeutically effective amount of a compound of formula I. In a still further aspect, the present invention provides a method of treating a subject suffering from a psychiatric disorder, comprising administering to the subject a therapeutically effective amount of a compound of formula I. In another embodiment, the present invention provides a method of treating a subject suffering from a drug addiction, such as an alcohol, amphetamine, cocaine, or opiate addiction.

DETAILED DESCRIPTION OF THE INVENTION

Definition of Substitutents

As used in the context of the present invention, the terms "halo" and "halogen" are used interchangeably and refer to fluorine, chlorine, bromine or iodine.

R1-R7 is short notation for the group consisting R1, R2, R3, R4, R5, R6, and R7. Subsets of R1-R7 are defined similarly, e.g. R5-R7 means the group consisting R5, R6, and R7.

The numbering of the substituents R1-R7 may also be specified by subscript, i.e. R1-R7. Similarly the number of atoms (e.g. carbon atoms) may either be indicated by C1-C6 or by $C_1$-$C_6$, i.e. one to six carbon atoms.

The term "$C_1$-$C_6$ alkyl" refers to a straight-chain or branched saturated hydrocarbon having from one to six carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl, and n-hexyl. The expression "$C_1$-$C_6$ hydroxyalkyl" refers to a $C_1$-$C_6$ alkyl group as defined above which is substituted with one hydroxy group. The term "halo($C_1$-$C_6$)alkyl" refers to a $C_1$-$C_6$ alkyl group as defined above which is substituted with up to three halogen atoms, such as trifluoromethyl.

The expression "$C_1$-$C_6$ alkoxy" refers to a straight-chain or branched saturated alkoxy group having from one to six carbon atoms, inclusive, with the open valency on the oxygen. Examples of such groups include, but are not limited to, methoxy, ethoxy, n-butoxy, 2-methyl-pentoxy and n-hexyloxy.

The term "$C_3$-$C_6$ cycloalkyl" includes cyclopropyl, cyclobutyl, cyclopentyl, cyclohexyl, cycloheptyl or cyclooctyl. The expression "$C_1$-$C_6$ alkyl($C_3$-$C_8$)cycloalkyl" refers to a $C_3$-$C_8$ cycloalkyl as defined above which is substituted with a straight-chain or branched $C_1$-$C_6$ alkyl. Examples of such groups include, but are not limited to, cyclopropylmethyl.

The term "heterocycloalkyl" refers to a four to eight membered ring containing carbon atoms and up to three N, O or S atoms. The open valency is on either the heteroatom or carbon atom. Examples of such groups include, but are not limited to, azetidinyl, oxetanyl, piperazinyl, morpholinyl, thiomorpholinyl and [1,4]diazepanyl. The term "hydroxyheterocycloalkyl" refers to a heterocycloalkyl as defined above which is substituted with one hydroxy group. The term "$C_1$-$C_6$ alkyl-heterocycloalkyl" refers to a heterocycloalkyl as defined above which is substituted with a $C_1$-$C_6$ alkyl group. Examples of such groups include, but are not limited to, tetrahydropyran-4-yl-methyl and 2-morpholin-4-yl-ethyl.

The term "aryl" refers to a phenyl ring, optionally substituted with halogen, $C_1$-$C_6$ alkyl, $C_1$-$C_6$ alkoxy or halo($C_1$-$C_6$) alkyl as defined above. Examples of such groups include, but are not limited to, phenyl and 4-chlorophenyl.

The term "$C_1$-$C_6$ arylalkyl" refers to an aryl as defined above which is substituted with a straight-chain or branched $C_1$-$C_6$ alkyl. Examples of such groups include, but are not limited to, benzyl and 4-chlorobenzyl.

Additionally, the present invention further provides certain embodiments of the invention, which are described below.

In one embodiment of the invention, HET is a heteroaromatic group of formula II containing 2 nitrogen atoms. In another embodiment of the invention, HET is a heteroaromatic group of formula II containing 3 nitrogen atoms. In yet another embodiment of the invention, HET is a heteroaromatic group of formula II containing 4 nitrogen atoms.

HET is preferably chosen among the following heteroaromatic groups, wherein "*" denotes the attachment point:

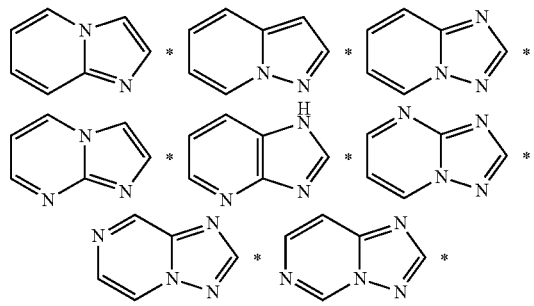

In a specific embodiment, HET is [1,2,4]triazolo[1,5-a]pyrazine. In a second specific embodiment, HET is [1,2,4]triazolo[1,5-a]pyridine. In a third specific embodiment, HET is imidazo[1,2-a]pyridine. In a fourth specific embodiment, HET is imidazo[4,5-b]pyrimidine. In a fifth specific embodiment, HET is pyrazolo[1,5-a]pyridine. In a sixth specific embodiment, HET is [1,2,4]Triazolo[1,5-a]pyrimidine. In a seventh specific embodiment, HET is [1,2,4]Triazolo[1,5-c]pyrimidine. In an eight specific embodiment, HET is imidazo[1,2-a]pyrimidine.

In another specific embodiment, HET is [1,2,4]triazolo[1,5-a]pyridine-6-carbonitrile. In another specific embodiment, HET is 1-methyl-1H-benzoimidazole. In another specific embodiment, HET is 1-phenyl-1H-benzoimidazole. In another specific embodiment, HET is 2-(6-chloro-benzoimidazol-1-yl)-ethanol. In another specific embodiment, HET is 5,7-dimethyl-[1,2,4]triazolo[1,5-a]pyridine. In another specific embodiment, HET is 5,7-dimethyl-imidazo[1,2-a]pyridine. In another specific embodiment, HET is 5-chloro-imidazo[1,2-a]pyridine. In another specific embodiment, HET is 5-methyl-imidazo[1,2-a]pyridine. In another specific embodiment, HET is 5-trifluoromethyl-imidazo[1,2-a]pyridine. In another specific embodiment, HET is 6-Bromo-5,7-dimethyl-[1,2,4]triazolo[1,5-a]pyridine. In another specific embodiment, HET is 6-bromo-7-methyl-[1,2,4]triazolo[1,5-a]pyridine. In another specific embodiment, HET is 6-chloro-8-methyl-[1,2,4]triazolo[1,5-a]pyridine. In another specific embodiment, HET is 6-chloro-imidazo[1,2-a]pyridine. In another specific embodiment, HET is 7-methyl-[1,2,4]triazolo[1,5-a]pyridine. In another specific embodiment, HET is 8-methyl-imidazo[1,2-a]pyridine. In another specific embodiment, HET is imidazo[1,2-a]pyridine-7-carbonitrile. In another specific embodiment, HET is 5,7-Dimethyl-[1,2,4]triazolo[1,5-a]pyrimidine.

Typically, HET is [1,2,4]Triazolo[1,5-a]pyrazine or 5,7-dimethyl-imidazo[1,2-a]pyrimidine or [1,2,4]Triazolo[1,5-c]pyrimidine.

In another embodiment of the invention L is —$CH_2$—$CH_2$—. In a further embodiment L is —$CH_2$—S—. In yet another embodiment L is —CH=CH—. In a still further embodiment L is —S—$CH_2$—.

In a further embodiment of the invention R1 and R2 are independently selected from the group consisting of H, OH, F, CH3, and OCH3; and R5, R6 and R7 are independently selected from the group consisting of H, CH3, and OCH3.

In a specific embodiment, HET is 5,8-dimethyl-[1,2,4]triazole[1,5-a]pyrazine; L is —$CH_2$—$CH_2$—; R1 and R2 are independently selected from the group consisting of H, OH, F, CH3, and OCH3, in particular R1 and R2 are H; n=0 and R3 and R4 are therefore absent; and R5, R6 and R7 are independently selected from the group consisting of H, CH3, and OCH3, in particular R5 is CH3, R6 is H and R7 is CH3.

In separate embodiments of the invention, the compound of formula I is selected among the following specific compounds, in the form of the free base, one or more tautomers thereof or a pharmaceutically acceptable acid addition salt thereof.

In a specific embodiment of any of the previously mentioned embodiments one or more of the hydrogen atoms of the compound are replaced by deuterium.

Table 1 lists compounds of the invention and the corresponding $IC_{50}$ values determined as described in the section "PDE10A inhibition assay". Each of the compounds constitutes an individual embodiment, of the present invention:

Pharmaceutically Acceptable Salts

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the

TABLE 1

Compounds of the invention and $IC_{50}$ values

| Compound | PDE10 IC50 (nM) |
|---|---|
| 2-[2-(5,8-Dimethyl-[1,2,4]triazolo[1,5-a]pyrazin-2-yl)-ethyl]-5H-imidazo[2,1-a]isoindole | 0.4 |
| 2-[2-(5,8-Dimethyl-[1,2,4]triazolo[1,5-a]pyridin-2-yl)-ethyl]-5H-imidazo[2,1-a]isoindole | 0.69 |
| 2-[2-(5-Methyl-[1,2,4]triazolo[1,5-a]pyridin-2-yl)-ethyl]-5H-imidazo[2,1-a]isoindole | 6.1 |
| 2-[2-(5,8-Dimethyl-[1,2,4]triazolo[1,5-a]pyrazin-2-yl)-vinyl]-5H-imidazo[2,1-a]isoindole | 4.4 |
| {2-[2-(5H-Imidazo[2,1-a]isoindol-2-yl)-ethyl]-5-methyl-[1,2,4]triazolo[1.5-a]pyrazin-8-yl}-methanol | 6.9 |
| 2-[2-(5,8-Dimethyl-[1,2,4]triazolo[1,5-a]pyrazin-2-yl)-ethyl]-7-fluoro-5H-imidazo[2,1-a]isoindole | 0.18 |
| 2-[2-(5,8-Dimethyl-[1,2,4]triazolo[1.5-a]pyrazin-2-yl)-ethyl]-5,6-dihydro-imidazo[2,1-a]isoquinoline | 0.81 |
| 2-[2-(5,8-Dimethyl-7-oxy-[1,2,4]triazolo[1,5-a]pyrazin-2-yl)-ethyl]-5H-imidazo[2,1-a]isoindole | 2.4 |
| 2-[2-(5,8-Dimethyl-[1,2,4]triazolo[1,5-a]pyrazin-2-yl)-ethyl]-8-fluoro-5H-imidazo[2,1-a]isoindole | 3.1 |
| 2-[2-(5,8-Dimethyl-[1,2,4]triazolo[1,5-a]pyrazin-2-yl)-ethyl]-7-methoxy-5H-imidazo[2,1-a]isoindole | 0.29 |
| 2-{2-[2-(5,8-Dimethyl-[1,2,4]triazolo[1,5-a]pyrazin-2-yl)-ethyl]-5H-imidazo[2,1-a]isoindol-5-yl}-propan-2-ol | 21 |
| 2-[2-(5,8-Dimethyl-[1,2,4]triazolo[1,5-a]pyrazin-2-yl)-ethyl]-6-fluoro-5H-imidazo[2,1-a]isoindole | 1.2 |
| 2-[2-(5,8-Dimethyl-[1,2,4]triazolo[1,5-a]pyrazin-2-yl)-ethyl]-9-fluoro-5H-imidazo[2,1-a]isoindole | 0.79 |
| 2-[2-(5,8-Dimethyl-[1,2,4]triazolo[1,5-a]pyrazin-2-yl)-ethyl]-8-methoxy-5H-imidazo[2,1-a]isoindole | 6.9 |
| 2-[2-(5,8-Dimethyl-[1,2,4]triazolo[1,5-a]pyrazin-2-yl)-ethyl]-6-methoxy-5H-imidazo[2,1-a]isoindole | 0.44 |
| 2-[2-(5,8-Bis(trideuteromethyl)-[1,2,4]triazolo[1,5-a]pyrazin-2-yl)-ethyl]-5,5-dideutero-5H-imidazo[2,1-a]isoindole | 0.4 |
| 2-[2-(5,8-Dimethyl-[1,2,4]triazolo[1,5-a]pyrazin-2-yl)-ethyl]-9-methoxy-5H-imidazo[2,1-a]isoindole | 0.44 |
| 2-[2-(5,8-Dimethyl-[1,2,4]triazolo[1,5-a]pyrazin-2-yl)-ethyl]-5H-imidazo[1',2':1,2]pyrrolo[3,4-b]pyridine | 46 |
| 2-[2-(5,8-Dimethyl-[1,2,4]triazolo[1,5-a]pyrazin-2-yl)-ethyl]-5H-imidazo[1',2':1,5]pyrrolo[3,4-b]pyridine | 3.8 |
| 2-([1,2,4]Triazolo[1,5-a]pyridin-2-ylsulfanylmethyl)-5H-imidazo[2,1-a]isoindole | 5300 |
| 2-[(5,7-dimethyl-[1,2,4]triazolo[1,5-a]pyrimidin-2-yl)sulfanylmethyl]-5H-imidazo[2,1-a]isoindole | 260 |
| 2-(5,8-Dimethyl-[1,2,4]triazolo[1,5-a]pyrazin-2-ylsulfanylmethyl)-5H-imidazo[2,1-a]isoindole | n.d. |

In a particular embodiment of the present invention the compounds of the present invention have an $IC_{50}$ value of less than 20 nM, such as in the range of 0.1-20 nM, particularly in the range of 0.1-10 nM, such as in the range of 0.1-5 nM or in the range of 0.1-1 nM.

8-halotheophyllines, for example 8-bromotheophylline and the like. Further examples of pharmaceutically acceptable inorganic or organic acid addition salts include the pharmaceutically acceptable salts listed in Berge, S. M. et al., J. Pharm. Sci. 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Pharmaceutical Compositions

The present invention further provides a pharmaceutical composition comprising a therapeutically effective amount of a compound of formula I and a pharmaceutically acceptable carrier or diluent. The present invention also provides a pharmaceutical composition comprising a therapeutically effective amount of one of the specific compounds disclosed in the Experimental Section herein and a pharmaceutically acceptable carrier or diluent.

The compounds of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

For parenteral routes such as intravenous, intrathecal, intramuscular and similar administration, typical doses are in the order of half the dose employed for oral administration.

The present invention also provides a process for making a pharmaceutical composition comprising admixing a therapeutically effective amount of a compound of formula I and at least one pharmaceutically acceptable carrier or diluent. In an embodiment, of the present invention, the compound utilized in the aforementioned process is one of the specific compounds disclosed in the Experimental Section herein.

The compounds of this invention are generally utilized as the free substance or as a pharmaceutically acceptable salt thereof. One example is an acid addition salt of a compound having the utility of a free base. When a compound of formula I contains a free base such salts are prepared in a conventional manner by treating a solution or suspension of a free base of formula I with a molar equivalent of a pharmaceutically acceptable acid. Representative examples of suitable organic and inorganic acids are described above.

For parenteral administration, solutions of the compounds of formula I in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of formula I may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of formula I and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tabletting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

Treatment of Disorders

As mentioned above, the compounds of formula I are PDE10A enzyme inhibitors and as such are useful to treat associated neurological and psychiatric disorders.

The invention thus provides a compound of formula I or a pharmaceutically acceptable acid addition salt thereof, as well as a pharmaceutical composition containing such a compound, for use in the treatment of a neurodegenerative disorder, psychiatric disorder or drug addiction in humans.

In one embodiment of the present invention, the neurodegenerative disorder or condition involves neurodegeneration of striatal medium spiny neurons in a human. In a specific embodiment of the present invention, the neurodegenerative disorder or condition is Huntington's disease. In a further embodiment the disorder is dyskinesia associated with dopamine agonist therapy.

In an embodiment the psychiatric disorder is selected from the group consisting of schizophrenia, for example of the paranoid, disorganized, catatonic, undifferentiated, or residual type; schizophreniform disorder, schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type.

This invention further provides a method of treating a drug addiction, for example an alcohol, amphetamine, cocaine, or opiate addiction, in a human, which method comprises administering to said human an amount of a compound of formula I effective in treating drug addiction.

The term "drug addiction", as used herein, means an abnormal desire for a drug and is generally characterized by motivational disturbances such a compulsion to take the desired drug and episodes of intense drug craving.

Drug addiction is widely considered a pathological state. The disorder of addiction involves the progression of acute drug use to the development of drug-seeking behavior, the vulnerability to relapse, and the decreased, slowed ability to respond to naturally rewarding stimuli. For example, The Diagnostic and Statistical Manual of Mental Disorders, Fourth Edition (DSM-IV) has categorized three stages of addiction: preoccupation/anticipation, binge/intoxication, and withdrawal/negative affect. These stages are characterized, respectively, everywhere by constant cravings and preoccupation with obtaining the substance; using more of the substance than necessary to experience the intoxicating effects; and experiencing tolerance, withdrawal symptoms, and decreased motivation for normal life activities.

Other disorders that can be treated according to the present invention are obsessive/compulsive disorders, non-insuline demanding diabetes mellitus (NIDDM), and Tourette's syndrome and other tic disorders as well as Attention Deficit/Hyperactivity Disorder (ADHD).

The compounds of formula I or pharmaceutically acceptable salts thereof may be used in combination with one or more other drugs (including typical and atypical antpsychotic agent) in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. The combinations, uses and methods of treatment of the invention may also provide advantages in treatment of patients who fail to respond adequately or who are resistant to other known treatments.

Such other drugs may be administered, by a route and in an amount commonly used therefore, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

The term "neuroleptic agent" as used herein refers to drugs, which have the effect on cognition and behaviour of antipsychotic agent drugs that reduce confusion, delusions, hallucinations, and psychomotor agitation in patients with psychoses. Also known as major tranquilizers and antipsychotic drugs, neuroleptic agents include, but are not limited to: typical antipsychotic drugs, including phenothiazines, further divided into the aliphatics, piperidines, and piperazines, thioxanthenes (e.g., cisordinol), butyrophenones (e.g., haloperidol), dibenzoxazepines (e.g., loxapine), dihydroindolones (e.g., molindone), diphenylbutylpiperidines (e.g., pimozide), and atypical antipsychotic drugs, including benzisoxazoles (e.g., risperidone), sertindole, olanzapine, quetiapine, osanetant and ziprasidone.

Particularly preferred neuroleptic agents for use in the invention are sertindole, olanzapine, risperidone, quetiapine, aripiprazole, haloperidol, clozapine, ziprasidone and osanetant.

As used herein, and unless otherwise indicated, a "neurodegenerative disorder or condition" refers to a disorder or condition that is caused by the dysfunction and/or death of neurons in the central nervous system. The treatment of these disorders and conditions can be facilitated by administration of an agent which prevents the dysfunction or death of neurons at risk in these disorders or conditions and/or enhances the function of damaged or healthy neurons in such a way as to compensate for the loss of function caused by the dysfunction or death of at-risk neurons. The term "neurotrophic agent" as used herein refers to a substance or agent that has some or all of these properties.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

It should be understood that the various aspects, embodiments, implementations and features of the invention mentioned herein may be claimed separately, or in any combination, as illustrated by the following non-limiting examples.

The present invention includes all modifications and equivalents of the subject-matter recited in the claims appended hereto, as permitted by applicable law.

EXPERIMENTAL SECTION

Preparation of the Compounds of the Invention

Compounds of the general formula I of the invention may be prepared as described in the following reaction schemes.

Compounds of formula I, wherein L is —CH$_2$—S—, can be prepared by the coupling of a nucleophile of formula III with an electrophile of formula IV, where Q is a leaving group, e.g. Cl, Br, I, methanesulfonyl, 4-toluenesulfonyl, as shown in scheme 1.

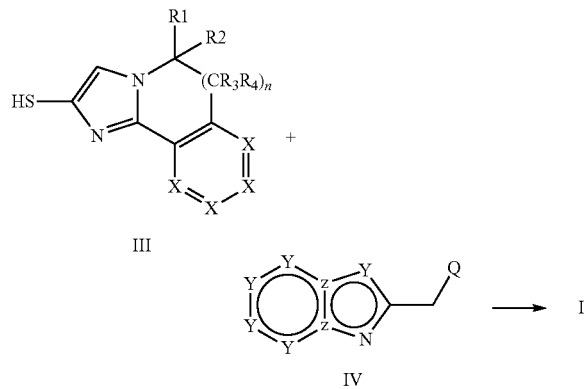

This reaction is typically carried out in a solvent such as 1-propanol, toluene, DMF, or acetonitrile, optionally in the presence of a carbonate base such as potassium carbonate or a tertiary amine base such as triethylamine or diisopropylethylamine (DIPEA), at a temperature ranging from about 0° C. to about 200° C., optionally under pressure in a closed vessel. Other suitable solvents include benzene, chloroform, dioxane, ethyl acetate, 2-propanol and xylene. Alternatively, solvent mixtures such as toluene/2-propanol can be used.

Thiol-compounds of formula III can be made by methods similar to those described in the literature e.g. *Journal of Heterocyclic Chemistry* 1977 14(5), 889-92, *Journal of the Chemical Society, Perkin Transactions 1: Organic and Bio-Organic Chemistry* 1979, 5, 1132-6, *Journal of the Chemical Society, Perkin Transactions 1: Organic and Bio-Organic Chemistry* 1997, 20, 2983-2988, *Organic & Biomolecular Chemistry* 2009, 7, 128-134.

Some electrophiles of formula IV are commercially available, and many others are known in the art, see for example JP 59176277 and US 2010016303. The electrophile IV, where Q is a leaving group, e.g. Cl, Br, I, methanesulfonyl, 4-toluenesulfonyl, can also be prepared by conversion of the corresponding primary alcohol to said leaving group by methods known to chemists skilled in the art. Said methods can for example be selected from reacting compounds of the corresponding primary alcohol with thionyl chloride, phosphorous trichloride, phosphorous tribromide, methanesulfonyl chloride, or 4-toluenesulfonyl chloride optionally in the presence of a suitable solvent, such as dichloromethane or 1,2-dichloroethane, and optionally in the presence of a base, such as triethylamine, diisopropylethylamine, or pyridine. Alternatively, electrophiles of formula IV can be prepared by reacting commercially available heteroaromatic amines with 1,3-dihaloacetones of, e.g. 1,3-dichloroacetone, in a suitable solvent, such as 1,2-dimethoxyethane or ethanol, at a suitable temperature, such as room temperature or reflux. Some electrophiles of formula IV are commercially available, and many others are known in the art, see for example Tsuchiya, T.; Sashida, H. *J. Chem. Soc., Chem. Commun.* 1980, 1109-1110; Tsuchiya, T.; Sashida, H; Konoshita, A. *Chem. Pharm. Bull.* 1983, 31, 4568-4572.

Compounds of formula I, wherein L is —S—CH$_2$—, can be prepared by the coupling of a nucleophile of formula V or Va with an electrophile of formula VI, where Q is a leaving group, e.g. Cl, Br, I, methanesulfonyl, 4-toluenesulfonyl, as shown in scheme 2. In the reaction between V and Va with VI, alkylation of the sulfur atom of V or Va with VI and ring closure to form the triazole ring both take place under the same reaction conditions in a one-pot procedure.

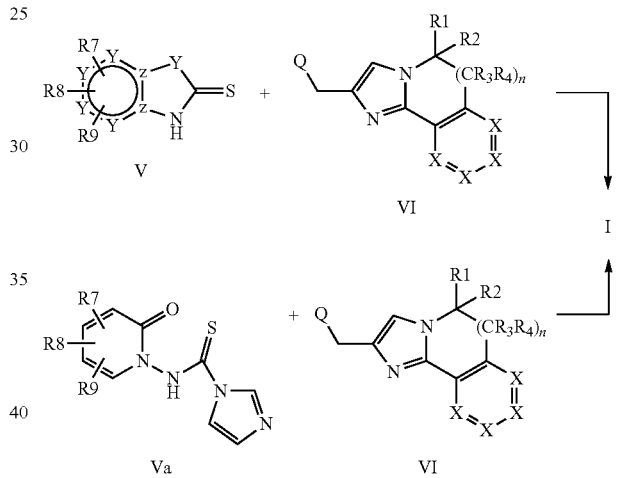

This reaction is typically carried out in a solvent such as 1-propanol, toluene, DMF, or acetonitrile, optionally in the presence of a carbonate base such as potassium carbonate or a tertiary amine base such as triethylamine or diisopropylethylamine (DIPEA), at a temperature ranging from about 0° C. to about 200° C., optionally under pressure in a closed vessel. Other suitable solvents include benzene, chloroform, dioxane, ethyl acetate, 2-propanol and xylene. Alternatively, solvent mixtures such as toluene/2-propanol can be used.

Compounds of formula V are either commercially available or can be prepared as described in the literature, see for example Brown et al. *Aust. J. Chem.* 1978, 31, 397-404; Yutilov et al. *Khim. Geter. Soedin.* 1988, 799-804; Wilde et al. *Bioorg. Med. Chem. Lett.* 1995, 5, 167-172; Kidwai et al. *J. Korean Chem. Soc.* 2005, 49, 288-291. Compounds of formula Va can be prepared as described in WO 96/01826 from the corresponding 1,2-diaminopyridines by reaction with thiocarbonyldiimidazole in a suitable solvent, such as chloroform, at a suitable temperature, such as room temperature or +40° C. The requisite 1,2-diaminopyridines are readily available from the corresponding commercially available 2-aminopyridines by reaction with a suitable N-amination reagent, such as O-(mesitylsulfonyl)hydroxylamine, in a suitable solvent, such as chloroform, at a suitable temperature, such as 0° C. or room temperature, see WO 96/01826.

Compounds of formula VI can be prepared as described in e.g. Venkatesan, A. et al. *ChemMedChem* 2008, 3, 1658-1661.

Compounds of formula I, wherein L is —CH=CH— or —CH$_2$—CH$_2$— can be prepared by the reaction sequence shown in scheme 3.

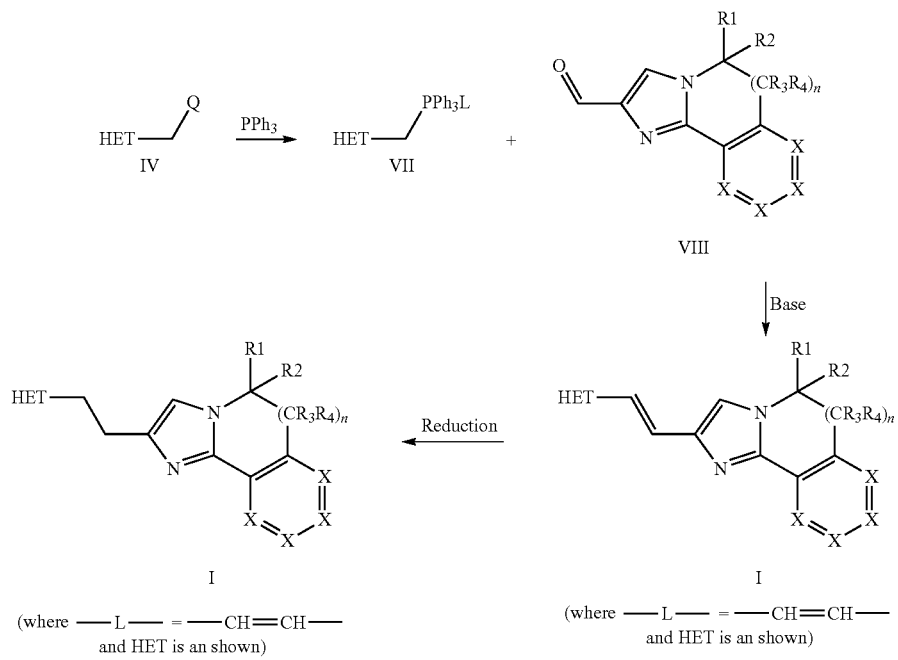

Specifically, compounds of formula I, wherein L is —CH$_2$—CH$_2$— can be prepared by reduction of an alkene of formula I, wherein L is —CH=CH—, by hydrogenation using a transition metal catalyst, such as palladium metal, together with a hydrogen source, such as hydrogen gas, ammonium hydrogen carbonate, or cyclohexadiene. Said alkenes of formula I, wherein L is —CH=CH— can be prepared by the Wittig reaction between a phosphonium salt of formula VII and an aldehyde of formula VIII in a suitable solvent, such as tetrahydrofuran, in the presence of a suitable base, such as 1,8-diazabicyclo[5.4.0]undec-7-ene. Phosphonium salt of formula VII are readily available by reaction of compounds of formula IV (see scheme 1 above) with triphenylphosphine by methods known to chemists skilled in the art. Aldehydes of formula VIII are available by methods described in the literature se e.g. Venkatesan, A. et al. *ChemMedChem* 2008, 3, 1658-1661.

General Methods

Analytical LC-MS data were obtained using the following method:

A PE Sciex API 150EX instrument equipped with atmospheric pressure photo ionisation and a Shimadzu LC-8A/SLC-10A LC system was used. Column: 4.6×30 mm Waters Symmetry C$_{18}$ column with 3.5 micro m particle size; Column temperature: 60° C.; Solvent system: A=water/trifluoroacetic acid (99.95:0.05) and B=methanol/trifluoroacetic acid (99.965:0.035); Method: Linear gradient elution with A:B=83:17 to 0:100 in 2.4 minutes and with a flow rate of 3.0 mL/minute.

Preparative LC-MS-purification was performed on a PE Sciex API 150EX instrument with atmospheric pressure chemical ionization. Column: 50×20 mm YMC ODS-A with 5 micro m particle size; Method: Linear gradient elution with A:B=80:20 to 0:100 in 7 minutes and with a flow rate of 22.7 mL/minute. Fraction collection was performed by split-flow MS detection.

$^1$H NMR spectra were recorded at 500.13 MHz on a Bruker Avance AV500 instrument or at 600.16 MHz on a Bruker Avance Ultrashield plus instrument. TMS was used as internal reference standard. Chemical shift values are expressed in ppm. The following abbreviations are used for multiplicity of NMR signals: s=singlet, d=doublet, t=triplet, q=quartet, qui=quintet, h=heptet, dd=double doublet, dt=double triplet, dq =double quartet, td=triplet of doublets, tt=triplet of triplets, m=multiplet, brs=broad singlet and br=broad signal.

Abbreviations are in accordance with to the ACS Style Guide: "The ACS Styleguide—A manual for authors and editors" Janet S. Dodd, Ed. 1997, ISBN: 0841234620

Preparation of Intermediates

5H-Imidazo[2,1-a]isoindole-2-carbaldehyde

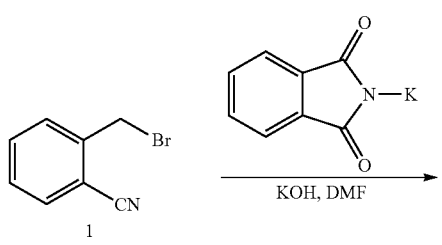

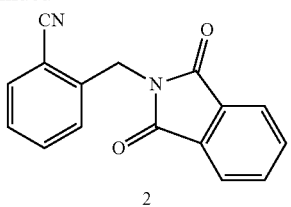

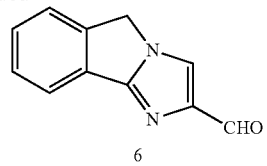

A solution of compound 1 (19 g, 0.097 mol) and potassium phthalimide (18 g, 0.097 mol) in DMF (100 mL) was heated at 100° C. for 1 hour. The mixture was poured into water (500 mL) and the solids filtered and washed with water. The solids were dried under vacuum to give compound 2 (21 g, yield: 65%) as a white solid. $^1$H NMR (400 MHz, CDCl$_3$): δ7.89-7.87 (m, 2H), 7.76-7.74 (m, 2H), 7.67 (d, J=6.8 Hz, 2H), 7.51 (t, J=7.6 Hz, 1H), 7.37 (t, J=8.0 Hz, 2H), 5.09 (s, 2H).

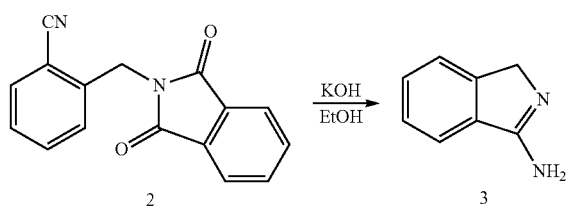

A mixture of compound 2 (21 g, 0.080 mol) and KOH (13 g, 0.230 mol) in EtOH (150 mL) was heated at 80° C. for 0.5 hour. The thick mixture was cooled and filtered. The filtrate was diluted with water (1 L) and extracted with EtOAc (200 mL×2). The combined organic layers were dried over Na$_2$SO$_4$ and concentrated to give crude compound 3 (8.05 g, 63%) as a brown solid.

A solution of crude compound 3 (8.05 g, 0.061 mol) and crude compound 5 (11.8 g, 0.061) was stirred at room temperature for 20 hours, then potassium carbonate (16.8 g, 122 mmol) was added to the mixture and heated to reflux for 2 hours. The reaction solution was concentrated, the residue was purified by column chromatography on silica gel (n-heptane/EtOAc, 1:1 to 100% EtOAc) to give 6 (2.00 g, yield: 6.95%) as a yellow solid. $^1$H NMR (400 MHz, CDCl$_3$): δ 9.89 (s, 1H), 7.88-7.83 (m, 2H), 7.45-7.43 (m, 2H), 7.39-7.37 (m, 1H), 4.93 (s, 2H).

The following intermediates were prepared in a similar way:

7-Fluoro-5H-imidazo[2,1-a]isoindole-2-carbaldehyde, NMR (600 MHz, CDCl$_3$): δ 9.93 (s, 1H), 7.92 (s, 1H), 7.91-7.89 (m, 1H), 7.26-7.21 (m, 2H), 5.03 (s, 2H). LC-MS (MH$^+$): m/z=203.0, t$_R$ (minutes)=0.53.

8-Fluoro-5H-imidazo[2,1-a]isoindole-2-carbaldehyde, $^1$H NMR (600 MHz, CDCl$_3$): δ 9.94 (s, 1H), 7.93 (s, 1H), 7.62 (dd, J=8.0, 2.4 Hz, 1H), 7.48 (dd, J=8.5, 4.5 Hz, 1H), 7.16 (td, J=8.5, 2.4 Hz, 1H), 5.02 (s, 2H). LC-MS (MH$^+$): m/z=203.1, t$_R$ (minutes) =0.64.

7-Methoxy-5H-imidazo[2,1-a]isoindole-2-carbaldehyde, $^1$H NMR (600 MHz, CDCl$_3$): 9.91 (s, 1H), 7.88 (s, 1H), 7.86-7.83 (m, 1H), 7.05-7.02 (m, 2H), 4.98 (s, 2H), 3.89 (s, 3H). LC-MS (MH$^+$): m/z=215.0, t$_R$ (minutes)=0.47.

5,6-Dihydro-imidazo[2,1-a]isoquinoline-2-carbaldehyde

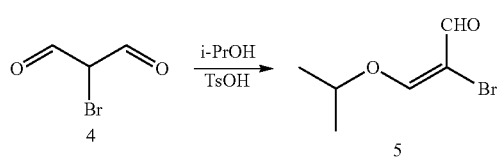

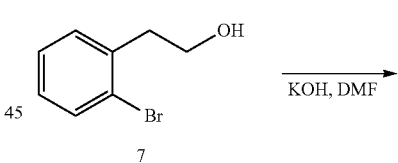

A mixture of compound 4 (3.9 g, 26.9 mmol), i-PrOH (7.8 mL), TsOH.H$_2$O (73 mg, 0.38 mmol) and hexane (49 mL) was distilled (atmospheric pressure, reaction temperature 67° C.) to remove the solvent, the remaining 27 mL of solution was further distilled in vacuum (~8.5 kPa, reaction temperature 25° C.) to afford the crude product 5 (5.0 g) as a brown liquid, which was unstable and used in the next step directly.

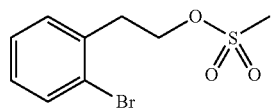

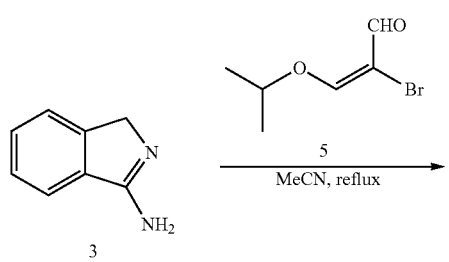

A solution of compound 7 (4.92 g, 0.037 mol) in toluene (100 mL) was treated with triethylamine (10.2 mL, 0.073 mol) and the solution cooled to 0° C. Methane sulfonyl chloride (2.87 mL, 0.037 mol) was added, after stirring at this temperature for 10 minutes the solution was allowed to warm to room temperature and stirred for 16 hours. The mixture was poured into water (250 mL) and extracted with DCM (250 mL×2). The combined organic layers were dried over MgSO$_4$ and concentrated to give crude compound 8 (7.05 g) as a brown liquid. $^1$H NMR (500 MHz, DMSO-d$_6$): δ7.59 (d, J=7.8 Hz, 2H), 7.44 (d, J=7.8 Hz, 2H), 7.38 (t, J=7.8 Hz, 2H), 7.23 (t, J=7.8 Hz, 1H), 4.43 (t, J=6.8 Hz, 2H), 3.14 (t, J=6.8 Hz, 2H), 3.12 (s, 3H).

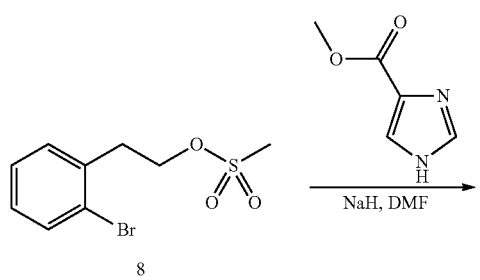

8

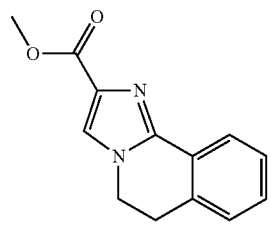

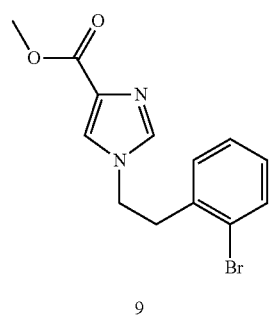

9

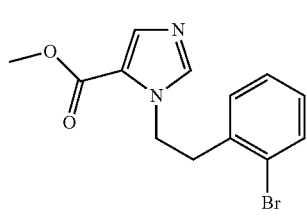

10

Methyl 4-imidazolecarboxylate (1.09 g, 8.62 mmol) was slowly added to a suspension of sodium hydride (60% dispersion in oil, 0.52 g, 13 mmol) in DMF (40 mL). The mixture was heated to 80° C. and stirred at this temperature for 1 hour. A solution of compound 8 (3.61 g, 12.90 mmol) in DMF (20 mL) was added dropwise to the reaction mixture at this temperature and the reaction mixture stirred a further 12 hours at 80° C. The cooled mixture was filtered, the volatiles removed in vacuo and the residue purified by column chromatography on silica gel (100% n-heptane to 100% EtOAc) to yield compound 10 (0.91 g, 34%) as a yellow semi solid first LC-MS (MH$^+$): m/z=311.3, $t_R$ (min,)=1.15 then compound 9 (1.38 g, yield: 51%) as a yellow solid LC-MS (MH$^+$): m/z=311.3, $t_R$ (minutes)=1.16.

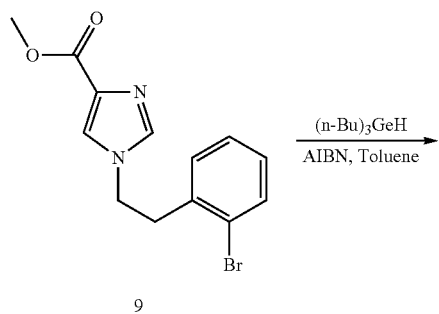

9

11

To a solution of 1-[2-(2-bromophenyl)ethyl]-1H-imidazole-4-carboxylic acid methyl ester (1.38 g, 4.46 mmol) in toluene (20 mL) degassed with argon and heated to 100° C. was added a solution of tributylgermanium hydride in toluene (10 mL) degassed with argon. 2,2'-Azo-bis-isobutyronitrile (0.88 g, 5.36 mmol) was added and the reaction stirred at 110° C. for 16 h. A further 2'-azo-bis-isobutyronitrile (0.88 g, 5.36 mmol) was added and the reaction stirred at 110° C. for 4 h. The reaction was quenched by pouring into 1M HCl solution (100 mL), the two phases were separated and the aqueous phase treated extracted with n-heptane (2×100 mL). The aqueous phase was basified with saturated sodium bicarbonate solution and extracted with DCM (3×100 mL). The combined organics were dried over MgSO$_4$, filtered and the volatiles removed in vacuo and the residue purified by column chromatography on silica gel (100% n-heptane to 100% EtOAc) to yield compound 11 (124 mg, 13%) LC-MS (MH$^+$): m/z=229.2, $t_R$ (minutes) =0.86.

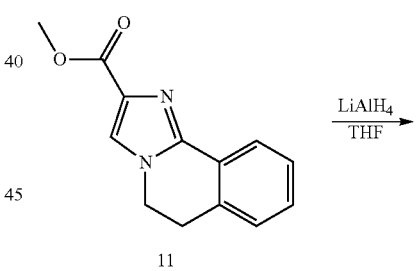

11

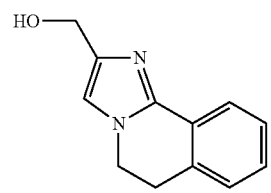

12

To a solution of 5,6-dihydroimidazo[2,1-a]isoquinoline-2-carboxylic acid methyl ester (210 mg, 0.92 mmol) in THF (9.6 mL) under an atmosphere of nitrogen was added a 1M solution of LiAlH$_4$ in THF (1.1 mL) and the solution stirred at room temperature for 2 h. Water (0.5 mL) was added followed by EtOAc (50 mL) and the solution dried with MgSO$_4$, filtered and the volatiles removed in vacuo to yield compound 12 (177 mg, 96%) LC-MS (MH$^+$): m/z=201.2, $t_R$ (minutes)= 0.29.

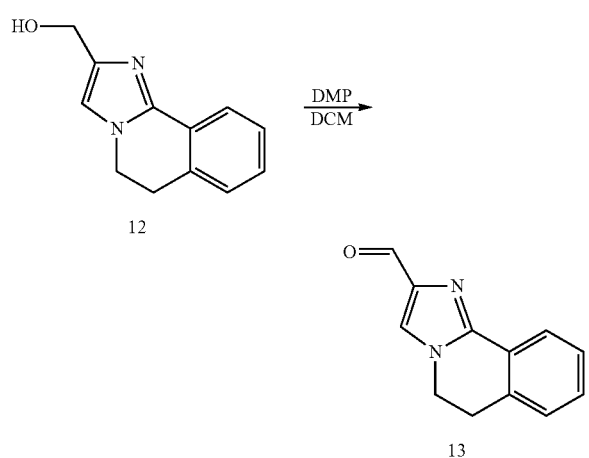

To a solution of (5,6-dihydroimidazo[2,1-a]isoquinolin-2-yl)methanol (177 mg, 0.88 mmol) in DCM (10 mL) under an atmosphere of argon was added Dess-Martin periodinane (41 mg, 0.97 mmol) and the solution stirred at room temperature for 2 h. The reaction was diluted with EtOAc (100 mL) and washed with saturated sodium bicarbonate solution (3×50 mL), brine (50 mL) then dried with $Na_2SO_4$, filtered and the volatiles removed in vacuo to yield crude compound 13 (165 mg, 94%) LC-MS (MH$^+$): m/z=199.0, $t_R$ (minutes)=0.55.

2-Chloromethyl-5,8-dimethyl-[1,2,4]triazolo[1,5-a]pyridine

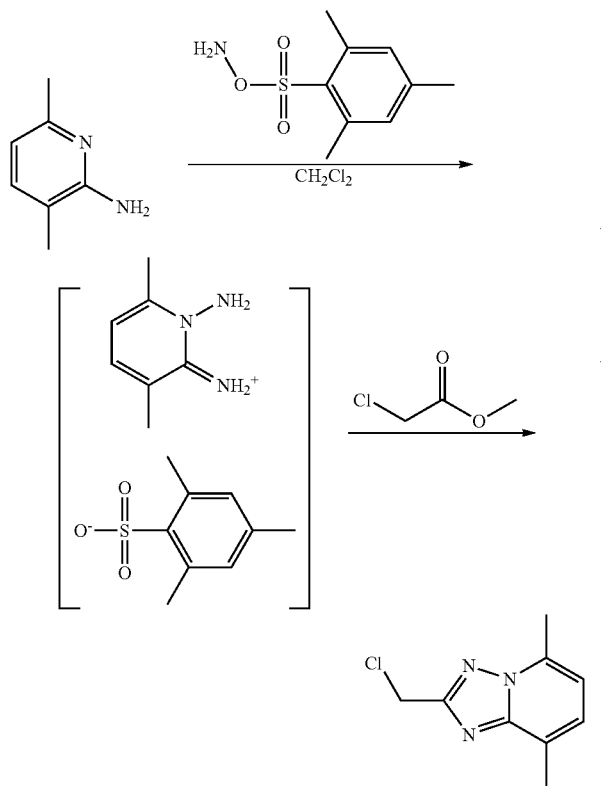

To a solution of 3,6-Dimethyl-2-pyridinamine (2.00 g, 16.4 mmol) in 50 mL of DCM was added dropwise a solution of hydroxylamine-2,4,6-Trimethyl-benzenesulfonate (4.22 g, 19.6 mmol) in 50 mL of $CH_2Cl_2$ at 0° C., and the mixture was stirred and allowed to warm to room temperature. The solvents were evaporated and the residue dissolved in 80 mL of MeOH then treated with DBU (3.43 mL, 22.9 mmol) and the solution stirred for 5 mins. After chloroacetic acid methyl ester (1.44 mL, 16.4 mmol) was added, the resultant mixture was stirred at room temperature for 48 h. After being concentrated under reduce pressure, the residue was diluted with water (100 mL) and extracted with EtOAc (3×100 mL). The combined organic layers were washed with water (50 mL), brine (50 mL), dried over $MgSO_4$, filtered, and concentrated under vacuum. The residue was purified by column chromatography on silica gel (petroleum ether/EtOAc=2/1) to give 2.65 g of 2-Chloromethyl-5,8-dimethyl-[1,2,4]triazolo[1,5-a]pyridine in 82% yield. LC-MS (MH$^+$): m/z=195.9, $t_R$ (minutes)=1.14

The following intermediates were prepared analogously:

2-Chloromethyl-5-methyl-[1,2,4]-triazolo[1,5-a]pyrazine from 2-amino-6-methylpyrazine. 28% yield, LC-MS: m/z=181.8 (MH$^+$), $t_R$=0.64 min 2-Chloromethyl-5,8-dimethyl-[1,2,4]triazolo[1,5-a]pyrazine from 2-amino-3,6-dimethylpyrazine. 60% yield, $^1$H NMR (500 MHz, CDCl$_3$): δ7.91 (s, 1H), 4.87 (s, 2H), 2.91 (s, 3H), 2.74 (s, 3H), LC-MS: m/z=196.9 (MH$^+$), $t_R$=0.64 min 6-Fluoro-5H-imidazo[2,1-a]isoindole-2-carbaldehyde

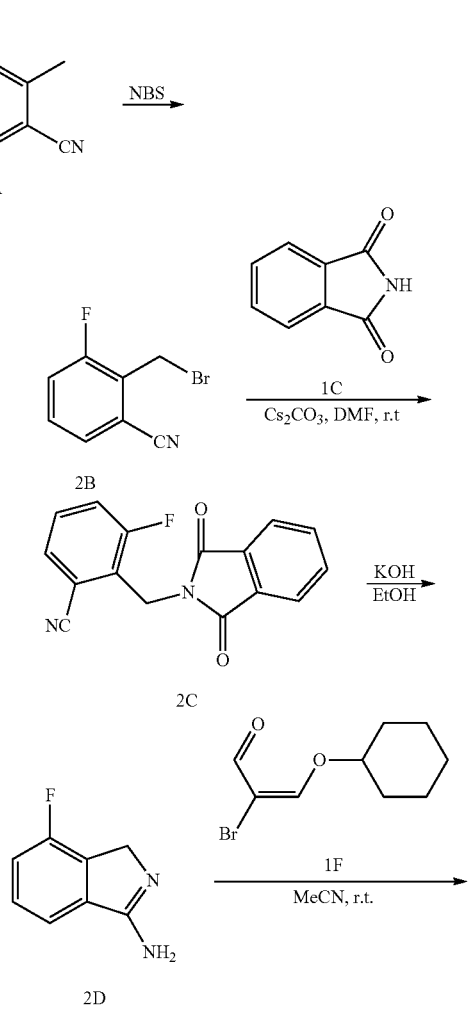

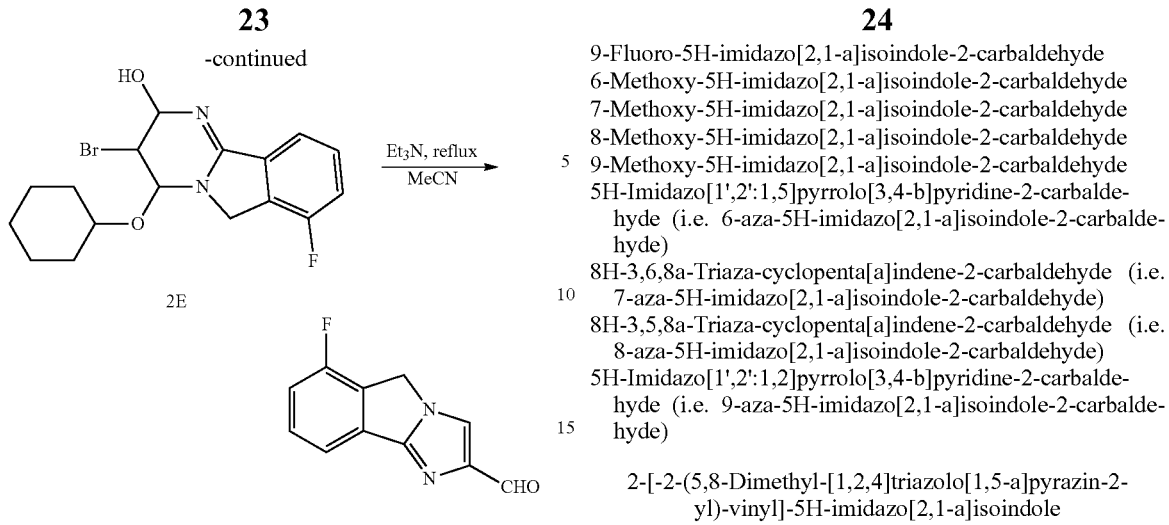

A solution of the compound 2A (50 g, 0.37 mol) in CCl₄ (500 mL) was added the NBS (72.5 g, 0.408 mol) and the AIBN (1.2 g, 0.037 mol), the reaction solution was refluxed for overnight, TLC indicated the reaction was completed, the reaction solution was filtered and concentrated in vacuum to give the crude product which was purified by flash silica chromatography eluting with petroleum ether/EtOAc (500:1) to give the desired compound 2B (30 g, yield: 40%) as a white solid.

To a solution of compound 2B (60 g, 0.28 mol) and compound 1C (78 g, 0.44 mol) in DMF (500 mL) was added Cs₂CO₃ (150 g, 0.46 mol). The mixture was stirred at r.t (12° C.) for 2 hours. TLC indicated that all the starting material 2B was consumed completely. The mixture was poured into water (2 L), the precipitated product was filtered, washed with water (500 mL) and methanol (500 mL) to give the product 2C (85 g, yield: 92%) as a white solid.

A mixture of compound 2C (130 g, 0.466 mol) and KOH (80 g, 1.43 mol) in EtOH (1.8 L) was heated at 90° C. for 0.5 hour. TLC showed that the reaction was completed. The mixture was cooled and filtered, the yellowish filtrate was concentrated in vacuum to give a brown solid, which was diluted with EtOAc (1 L) and water (300 mL), the aqueous layer was extracted by EtOAc (300 mL×5), the combined organic layer was washed by brine (300 mL), dried over anhydrous Na₂SO₄, concentrated in vacuum to give the product 2D (65 g, crude) as brown solid, which is pure enough for next step reaction. A mixture of compound 2D (25 g, crude) and compound 1F (43 g, 0.185 mol) in dry CH₃CN (500 mL) was stirred at r.t. (27° C.) overnight. The resulting mixture was filtered and washed with MeCN, and dried in vacuum over to afford compound 2E (37 g, yield: 85%). A solution of compound 2E (23 g, 60 mmol) and Et₃N (7.27 g, 72 mmol) in dry CH₃CN (400 mL) was stirred at 90° C.-100° C. reflux for 18 hours. The reaction solution was concentrated. The residue was diluted with EtOAc, and washed with 20% aqueous potassium hydrogen carbonate solution. After filtration through a pad of Celite, the organic layer was dried (MgSO₄) and concentrated in vacuum. The residue was purified by silica column chromatography (eluted with PE:EtOAc=5:1) to give 6-Fluoro-5H-imidazo[2,1-a]isoindole-2-carbaldehyde (1.1 g, yield: 10%) as a yellowish solid. ¹H NMR (CDCl₃, 400 MHz): δ9.9 (s, 1H), 7.89 (s, 1H), 7.69 (d, J=7.6 Hz, 1H), 7.50-7.44 (m, 1H), 7.11 (m, 1H), 5.04 (s, 2H).

The following intermediates were made in a similar way:
5H-imidazo[2,1-a]isoindole-2-carbaldehyde
7-Fluoro-5H-imidazo[2,1-a]isoindole-2-carbaldehyde
8-Fluoro-5H-imidazo[2,1-a]isoindole-2-carbaldehyde
9-Fluoro-5H-imidazo[2,1-a]isoindole-2-carbaldehyde
6-Methoxy-5H-imidazo[2,1-a]isoindole-2-carbaldehyde
7-Methoxy-5H-imidazo[2,1-a]isoindole-2-carbaldehyde
8-Methoxy-5H-imidazo[2,1-a]isoindole-2-carbaldehyde
9-Methoxy-5H-imidazo[2,1-a]isoindole-2-carbaldehyde
5H-Imidazo[1',2':1,5]pyrrolo[3,4-b]pyridine-2-carbaldehyde (i.e. 6-aza-5H-imidazo[2,1-a]isoindole-2-carbaldehyde)
8H-3,6,8a-Triaza-cyclopenta[a]indene-2-carbaldehyde (i.e. 7-aza-5H-imidazo[2,1-a]isoindole-2-carbaldehyde)
8H-3,5,8a-Triaza-cyclopenta[a]indene-2-carbaldehyde (i.e. 8-aza-5H-imidazo[2,1-a]isoindole-2-carbaldehyde)
5H-Imidazo[1',2':1,2]pyrrolo[3,4-b]pyridine-2-carbaldehyde (i.e. 9-aza-5H-imidazo[2,1-a]isoindole-2-carbaldehyde)

2-[-2-(5,8-Dimethyl-[1,2,4]triazolo[1,5-a]pyrazin-2-yl)-vinyl]-5H-imidazo[2,1-a]isoindole

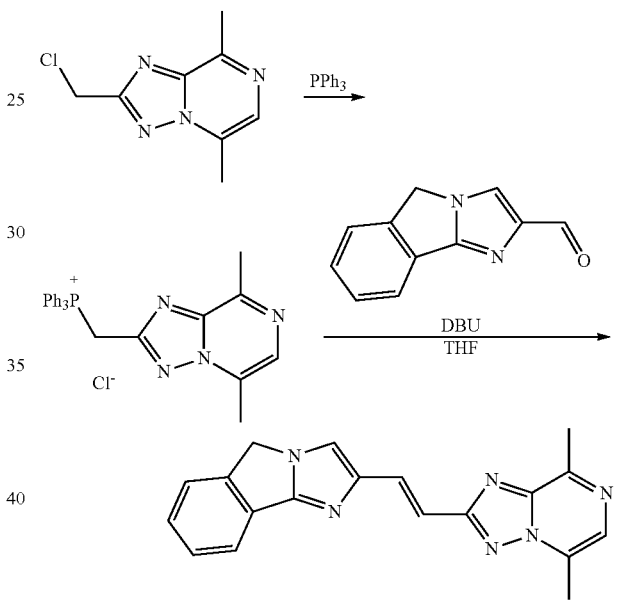

A solution of 2-chloromethyl-5,8-dimethyl-[1,2,4]triazolo[1,5-a]pyrazine (1.351 g, 6.87 mmol) and triphenylphosphine (1.80 g, 6.87 mmol) in acetonitrile 150 mL was heated at reflux for 12 h. The solvents were removed in vacuo and the residue slurried in ether, filtered and dried to yield (5,8-Dimethyl-[1,2,4]triazolo[1,5-a]pyrazin-2-ylmethyl)-triphenyl-phosphonium; chloride as an off white solid (2.412 g, 74.9%). LC-MS: m/z=423.2 ([M-Cl]⁺), $t_R$=0.86 minutes, method A.

A solution of 5H-Imidazo[2,1-a]isoindole-2-carbaldehyde (150 mg, 0.81 mmol) in dry THF (5.3 mL) was added to (5,8-Dimethyl-[1,2,4]triazolo[1,5-a]pyrazin-2-ylmethyl)-triphenyl-phosphonium chloride (374 mg, 0.81 mmol) under argon and 1,8-diazabicyclo[5.4.0]undec-7-ene (120 micro L, 0.81 mmol) was added. The reaction mixture was stirred at room temperature for 12 hours after which it was evaporated onto silica gel (2 g). Silica gel chromatography (gradient elution; A:B 100:0 to 0:100, where A is ethyl acetate and B is 10% MeOH in ethyl acetate) afforded the title compound as a mixture of the cis and trans isomers (139 mg, 52%). LC-MS: m/z=329.3 (MH⁺), $t_R$=0.96 minutes.

The following intermediates were prepared in a similar manner:

2-[-2-(5,8-Dimethyl-[1,2,4]triazolo[1,5-a]pyrazin-2-yl)-vinyl]-6-fluoro-5H-imidazo[2,1-a]isoindole
2-[-2-(5,8-Dimethyl-[1,2,4]triazolo[1,5-a]pyrazin-2-yl)-vinyl]-7-fluoro-5H-imidazo[2,1-a]isoindole
2-[-2-(5,8-Dimethyl-[1,2,4]triazolo[1,5-a]pyrazin-2-yl)-vinyl]-8-fluoro-5H-imidazo[2,1-a]isoindole
2-[-2-(5,8-Dimethyl-[1,2,4]triazolo[1,5-a]pyrazin-2-yl)-vinyl]-9-fluoro-5H-imidazo[2,1-a]isoindole
2-[-2-(5,8-Dimethyl-[1,2,4]triazolo[1,5-a]pyrazin-2-yl)-vinyl]-6-methoxy-5H-imidazo[2,1-a]isoindole
2-[-2-(5,8-Dimethyl-[1,2,4]triazolo[1,5-a]pyrazin-2-yl)-vinyl]-7-methoxy-5H-imidazo[2,1-a]isoindole
2-[-2-(5,8-Dimethyl-[1,2,4]triazolo[1,5-a]pyrazin-2-yl)-vinyl]-8-methoxy-5H-imidazo[2,1-a]isoindole
2-[-2-(5,8-Dimethyl-[1,2,4]triazolo[1,5-a]pyrazin-2-yl)-vinyl]-9-methoxy-5H-imidazo[2,1-a]isoindole
2-[(E)-2-(5,8-Dimethyl-[1,2,4]triazolo[1,5-a]pyrazin-2-yl)-vinyl]-5H-imidazo[1',2':1,2]pyrrolo[3,4-b]pyridine
2-[(E)-2-(5,8-Dimethyl-[1,2,4]triazolo[1,5-a]pyrazin-2-yl)-vinyl]-5H-imidazo[1',2':1,5]pyrrolo[3,4-b]pyridine The invention disclosed herein is further illustrated by the following non-limiting examples.

Example 1

2-[-2-(5,8-Dimethyl-[1,2,4]triazolo[1,5-a]pyrazin-2-yl)-vinyl]-5H-imidazo[2,1-a]isoindole

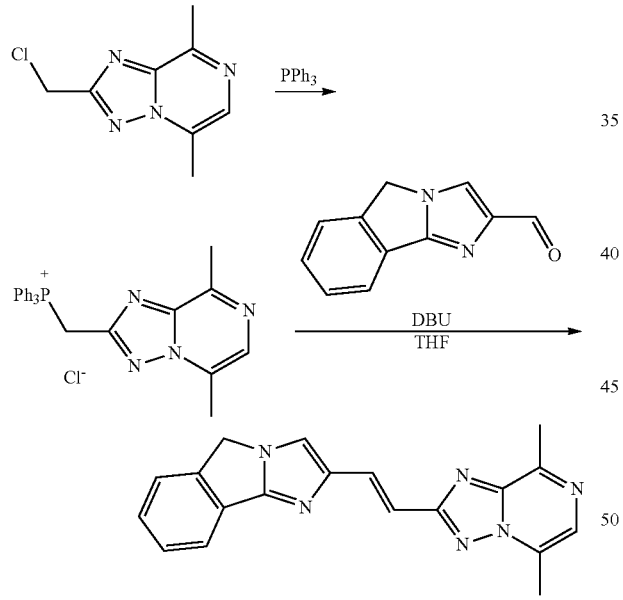

A solution of 2-chloromethyl-5,8-dimethyl-[1,2,4]triazolo[1,5-a]pyrazine (1.351 g, 6.87 mmol) and triphenylphosphine (1.80 g, 6.87 mmol) in acetonitrile 150 mL was heated at reflux for 12 h. The solvents were removed in vacuo and the residue slurried in ether, filtered and dried to yield (5,8-Dimethyl-[1,2,4]triazolo[1,5-a]pyrazin-2-ylmethyl)-triphenyl-phosphonium; chloride as an off white solid (2.412 g, 74.9%). LC-MS: m/z=423.2 ([M-Cl]$^+$), $t_R$=0.86 minutes, method A.

A solution of 5H-Imidazo[2,1-a]isoindole-2-carbaldehyde (150 mg, 0.81 mmol) in dry THF (5.3 mL) was added to (5,8-Dimethyl-[1,2,4]triazolo[1,5-a]pyrazin-2-ylmethyl)-triphenyl-phosphonium chloride (374 mg, 0.81 mmol) under argon and 1,8-diazabicyclo[5.4.0]undec-7-ene (120 micro L, 0.81 mmol) was added. The reaction mixture was stirred at room temperature for 12 hours after which it was evaporated onto silica gel (2 g). Silica gel chromatography (gradient elution; A:B 100:0 to 0:100, where A is ethyl acetate and B is 10% MeOH in ethyl acetate) afforded the title compound as a mixture of the cis and trans isomers (139 mg, 52%). LC-MS: m/z=329.3 (MH$^+$), $t_R$=0.96 minutes.

Example 2

Synthesis of 2-[-2-(5,8-Dimethyl-[1,2,4]triazolo[1,5-a]pyrazin-2-yl)-ethyl]-5H-imidazo[2,1-a]isoindole

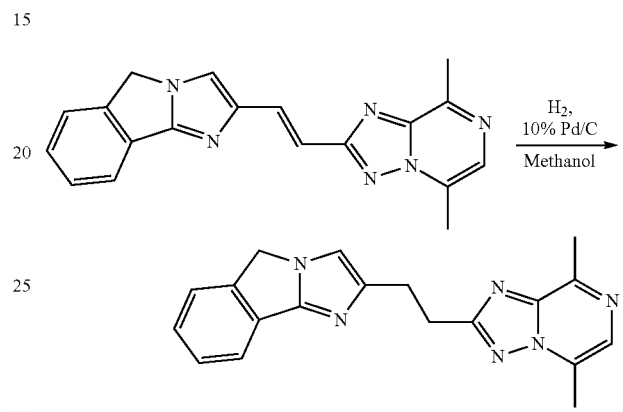

To a solution of 2-[-2-(5,8-Dimethyl-[1,2,4]triazolo[1,5-a]pyrazin-2-yl)-vinyl]-5H-imidazo[2,1-a]isoindole (139 mg, 0.423 mmol) in methanol (100 mL) was added 10% palladium on carbon (27 mg). A current of hydrogen gas was bubbled through, and the reaction was kept under an atmosphere of hydrogen overnight with stirring. After filtration the organics were evaporated onto silica gel (2 g). Chromatography (gradient elution; A:B 100:0 to 0:100, where A is ethyl acetate and B is 10% MeOH in ethyl acetate) afforded the title compound as a white solid (50.6 mg, 36%). $^1$H NMR (500 MHz, CDCl$_3$): δ 7.86-7.82 (m, 2H), 7.46-7.42 (m, 2H), 7.33 (t, J=7.5 Hz, 1H), 7.02 (s, 1H), 4.84 (s, 2H), 3.44 (dd, J=8.9, 6.6 Hz, 2H), 3.33 (dd, J=8.9, 6.6 Hz, 2H), 2.91 (s, 3H), 2.73 (s, 3H). LC-MS: m/z=331.0 (MH$^+$), $t_R$=0.74 minutes.

Example 3

2-[2-(5,8-Dimethyl-[1,2,4]-triazolo[1,5-a]pyrazin-2-yl)-ethyl]-5,6-dihydroimidazo[2,1-a]isoquinoline

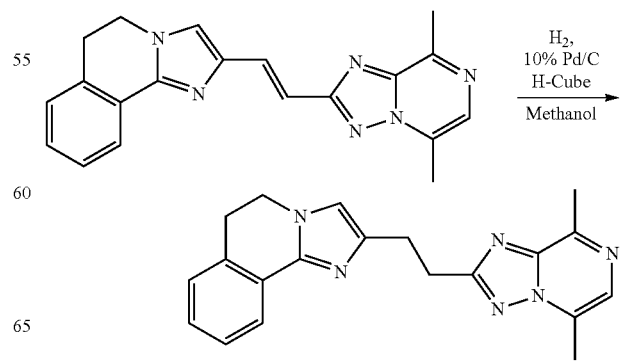

A solution of 2-[2-(5,8-Dimethyl-[1,2,4]triazolo[1,5-a]pyrazin-2-yl)-ethyl]-5,6-dihydro-imidazo[2,1-a]isoquinoline (210 mg, 0.61 mmol) in methanol:DCM (2:1, v/v, 30 mL) was passed through a H-Cube® Continuous-flow Hydrogenation Reactor (ThalesNano) at a flow rate of 1 mL/min through a small cartridge of 10% Pd/C (THS01111) with an internal temperature of 25° C. and 1 bar of hydrogen pressure. Evaporation of the volatiles afforded the title compound (75 mg, 19%). $^1$H NMR (600 MHz, CDCl$_3$): δ 8.02 (dd, J=7.7, 1.0 Hz, 1H), 7.83 (s, 1H), 7.33 (ddd, J=7.7, 1.3, 0.7 Hz, 1H), 7.26 (td, J=7.4, 1.3 Hz, 1H), 7.21 (dd, J=7.4, 0.7 Hz, 1H), 6.73 (s, 1H), 4.10 (t, J=6.9 Hz, 2H), 3.41 (dd, J=9.6, 6.5 Hz, 2H), 3.28 (dd, J=9.6, 6.5 Hz, 2H), 3.13 (t, J=6.9 Hz, 2H), 2.90 (s, 3H), 2.72 (s, 3H). LC-MS: m/z=345.1 (MH$^+$), $t_R$=0.83 minutes The Following compounds were prepared analogously:

2-[2-(5,8-Dimethyl-[1,2,4]triazolo[1,5-a]pyridin-2-yl)-ethyl]-5H-imidazo[2,1-a]isoindole, $^1$H NMR (600 MHz, DMSO): δ 7.67 (d, J=7.5 Hz, 1H), 7.57 (d, J=7.5 Hz, 1H), 7.44 (t, J=7.5 Hz, 1H), 7.38-7.32 (m, 2H), 7.27 (s, 1H), 6.92 (d, J=7.2 Hz, 1H), 4.99 (s, 2H), 3.23-3.16 (m, 2H), 3.09 (dd, J=9.7, 6.3 Hz, 2H), 2.67 (s, 3H). LC-MS: m/z=330.2 (MH$^+$), $t_R$=0.91 minutes 2-[2-(5-Methyl-[1,2,4]triazolo[1,5-a]pyridin-2-yl)-ethyl]-5H-imidazo[2,1-a]isoindole, $^1$H NMR (600 MHz, DMSO): δ 7.67 (d, J=7.5 Hz, 1H), 7.63 (d, J=8.8 Hz, 1H), 7.59-7.52 (m, 2H), 7.44 (t, J=7.5 Hz, 1H), 7.35 (t, J=7.5 Hz, 1H), 7.26 (s, 1H), 7.03 (d, J=7.0 Hz, 1H), 4.98 (s, 2H), 3.20 (dd, J=9.5, 6.4 Hz, 2H), 3.09 (dd, J=9.5, 6.4 Hz, 2H), 2.72 (s, 3H). LC-MS: m/z=315.7 (MH$^+$), $t_R$=0.78 minutes 2-[-2-(5,8-Dimethyl-[1,2,4]triazolo[1,5-a]pyrazin-2-yl)-ethyl]-7-fluoro-5H-imidazo[2,1-a]isoindole, $^1$H NMR (600 MHz, CDCl$_3$): δ 7.82 (d, J=1.0 Hz, 1H), 7.76 (dd, J=8.3, 5.0 Hz, 1H), 7.16-7.11 (m, 2H), 6.99 (s, 1H), 4.81 (s, 2H), 3.49-3.37 (m, 2H), 3.33-3.22 (m, 2H), 2.89 (s, 3H), 2.70 (s, 3H). LC-MS: m/z=349.1 (MH$^+$), $t_R$=0.80 minutes 2-[-2-(5,8-Dimethyl-[1,2,4]triazolo[1,5-a]pyrazin-2-yl)-ethyl]-8-fluoro-5H-imidazo[2,1-a]isoindole, $^1$H NMR (600 MHz, CDCl$_3$): δ 7.82 (d, J=0.8 Hz, 1H), 7.50 (dd, J=8.3, 2.4 Hz, 1H), 7.37 (dd, J=8.3, 4.6 Hz, 1H), 7.02-6.99 (m, 2H), 4.80 (s, 2H), 3.41 (dd, J=9.0, 6.5 Hz, 2H), 3.31 (dd, J=9.0, 6.5 Hz, 2H), 2.89 (s, 3H), 2.71 (s, 3H). LC-MS: m/z=349.1 (MH$^+$), $t_R$=0.80 minutes 2-[-2-(5,8-Dimethyl-[1,2,4]triazolo[1,5-a]pyrazin-2-yl)-ethyl]-7-methoxy-5H-imidazo[2,1-a]isoindole, $^1$H NMR (600 MHz, CDCl$_3$): δ 7.82 (d, J=0.7 Hz, 1H), 7.73 (d, J=8.4 Hz, 1H), 7.00-6.93 (m, 3H), 4.78 (s, 2H), 3.86 (s, 3H), 3.41 (dd, J=9.0, 6.6 Hz, 2H), 3.29 (dd, J=9.0, 6.6 Hz, 2H), 2.89 (s, 3H), 2.71 (s, 3H). LC-MS: m/z=361.2 (MH$^+$), $t_R$=0.87 minutes 2-[2-(5,8-Dimethyl-[1,2,4]triazolo[1,5-a]pyrazin-2-yl)-ethyl]-7-methoxy-5H-imidazo[2,1-a]isoindole, LC-MS: m/z=361.2 (MH+). Rt=0.87 min.; method=131

2-{2-[2-(5,8-Dimethyl-[1,2,4]-triazolo[1,5-a]pyrazin-2-yl)-ethyl]-5H-imidazo[2,1-a]isoindol-5-yl}-propan-2-ol, LC-MS: m/z=389.2 (MH+). Rt=0.88 min.; method=131

2-[2-(5,8-Dimethyl-[1,2,4]-triazolo[1,5-a]pyrazin-2-yl)-ethyl]-6-fluoro-5H-imidazo[2,1-a]isoindole, LC-MS: m/z=349.1 (MH+). Rt=0.78 min.; method=131

2-[2-(5,8-Dimethyl-[1,2,4]triazolo[1,5-a]pyrazin-2-yl)-ethyl]-9-fluoro-5H-imidazo[2,1-a]isoindole, LC-MS: m/z=349.1 (MH+). Rt=0.74 min.; method=131

2-[2-(5,8-Dimethyl-[1,2,4]triazolo[1,5-a]pyrazin-2-yl)-ethyl]-8-methoxy-5H-imidazo[2,1-a]isoindole, LC-MS: m/z=361.2 (MH+). Rt=0.85 min.; method=131

2-[2-(5,8-Dimethyl-[1,2,4]triazolo[1,5-a]pyrazin-2-yl)-ethyl]-6-methoxy-5H-imidazo[2,1-a]isoindole, LC-MS: m/z=361.2 (MH+). Rt=0.87 min.; method=131

2-[2-(5,8-Dimethyl-[1,2,4]triazolo[1,5-a]pyrazin-2-yl)-ethyl]-9-methoxy-5H-imidazo[2,1-a]isoindole, LC-MS: m/z=361.2 (MH+). Rt=0.85 min.; method=131

2-[2-(5,8-Dimethyl-[1,2,4]triazolo[1,5-a]pyrazin-2-yl)-ethyl]-5H-imidazo[1',2':1,2]pyrrolo[3,4-b]pyridine, LC-MS: m/z=332.1 (MH+). Rt=0.62 min.; method=131

2-[2-(5,8-Dimethyl-[1,2,4]triazolo[1,5-a]pyrazin-2-yl)-ethyl]-5H-imidazo[1',2'1,5]pyrrolo[3,4-b]pyridine, LC-MS: m/z=332.2 (MH+). Rt=0.48 min.; method=131

Example 4

Synthesis of 2-[-2-(5,8-Dimethyl-7-oxy-[1,2,4]triazolo[1,5-a]pyrazin-2-yl)-ethyl]-5H-imidazo[2,1-a]isoindole

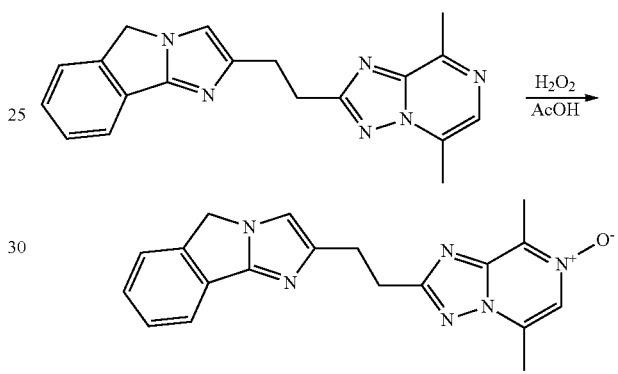

A solution of 2-[-2-(5,8-Dimethyl-[1,2,4]triazolo[1,5-a]pyrazin-2-yl)-ethyl]-5H-imidazo[2,1-a]isoindole (500 mg, 1.51 mmol) in AcOH (5 mL) was treated with 35% aqueous hydrogen peroxide (1.3 mL, 15.1 mmol) and the solution stirred at 40° C. for 12 h. The volatiles were removed in vacuo and the crude oil dissolved in water (10 mL) and basified to pH 10 with 2N NaOH solution. The solids were filtered, washed with water and dried at 40° C. to yield the title compound as an off white solid (101 mg, 20%). $^1$H NMR (500 MHz, CDCl$_3$): δ 7.85 (d, J=7.6 Hz, 1H), 7.70 (s, 1H), 7.49-7.39 (m, 2H), 7.34 (t, J=7.5 Hz, 1H), 7.02 (s, 1H), 4.85 (s, 2H), 3.38 (dd, J=8.8, 6.1 Hz, 2H), 3.34-3.23 (m, 2H), 2.80 (s, 3H), 2.70 (s, 3H). LC-MS: m/z=346.9 (MH$^+$), $t_R$=0.53 minutes Example 5

Synthesis of {2-[2-(5H-Imidazo[2,1-a]isoindol-2-yl)-ethyl]-5-methyl-[1,2,4]triazolo[1,5-a]pyrazin-8-yl}-methanol

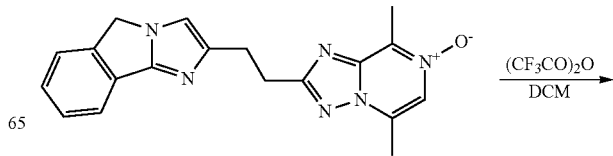

-continued

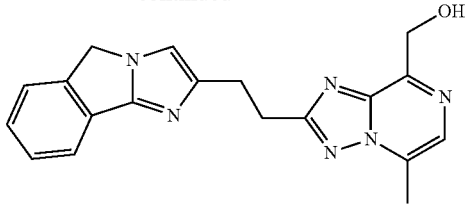

A solution of 2-[-2-(5,8-Dimethyl-7-oxy-[1,2,4]triazolo[1,5-a]pyrazin-2-yl)-ethyl]-5H-imidazo[2,1-a]isoindole (91 mg, 0.26 mmol) in DCM (5 mL) was treated with trifluoroacetic anhydride (93 μL, 0.66 mmol) and the solution stirred at room temperature for 2 h. The volatiles were removed in vacuo and the residue dissolved in DCM (10 mL) and saturated sodium carbonate solution (10 mL) was added. The mixture was stirred vigorously for 3 h. The phases were separated and the aqueous phase extracted with DCM (2×20 mL). The combine organics were washed with water, brine- and dried over MgSO$_4$. After evaporation of the volatiles the residue was purified by prep LCMS to yield the title compound as an off white solid (27 mg, 20%). $^1$H NMR (600 MHz, CDCl$_3$): δ 8.22-8.15 (m, 1H), 7.94 (s, 1H), 7.68-7.54 (m, 3H), 7.21 (s, 1H) 5.14 (s, 2H), 5.10 (s, 2H), 3.47 (bs, 4H), 2.75 (s, 3H), 2.66 (s, 1H). LC-MS: m/z=346.9 (MH$^+$), t$_R$=0.61 minutes Example 6

2-([1,2,4]Triazolo[1,6-a]pyridin-2-ylsulfanylmethyl)-5H-imidazo[2,1-a]isoindole

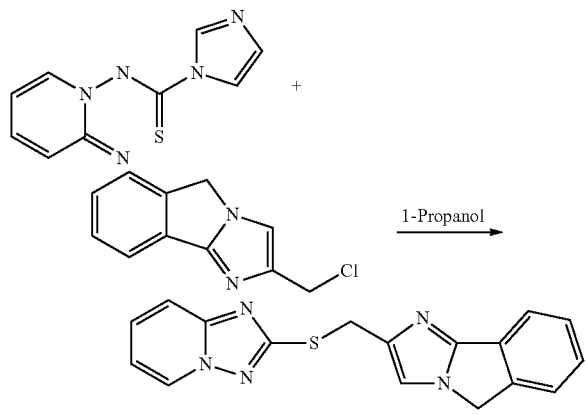

An adaptation of the method described in WO 96/01826 was used. Imidazole-1-carbothioic acid (2-imino-2H-pyridin-1-yl)-amide (200 mg, 1.37 mmol) and 2-Chloromethyl-5H-imidazo[2,1-a]isoindole (300 mg, 1.46 mmol) were dissolved in 1-propanol (25 mL) and the mixture was heated to reflux for 2 hours. The solvent was removed under reduced pressure and the residue dissolved in dichloromethane. The solution was washed with water and the organic layer was dried over Na$_2$SO$_4$ and concentrated. The residue was purified by chromatography on silica gel to afford the title compound (273 mg, 62%) as a yellow solid. LC-MS: m/z=321.1 (MH$^+$), t$_R$=1.40 min, method B.

The following compounds of the invention were prepared analogously:

2-[(5,7-dimethyl-[1,2,4]triazolo[1,5-a]pyrimidin-2-yl)sulfanylmethyl]-5H-imidazo[2,1-a]isoindole; LC-MS: m/z=349.1 (MH$^+$), t$_R$=1.59 min, method B.

2-(5,8-Dimethyl-[1,2,4]triazolo[1,5-a]pyrazin-2-ylsulfanylmethyl)-5H-imidazo[2,1-a]isoindole Example 7

Synthesis of 2-[-2-(5,8-Bis(trideuteromethyl-[1,2,4]triazolo[1,5-a]pyrazin-2-yl)-ethyl]-5,5-dideutero-5H-imidazo[2,1-a]isoindole

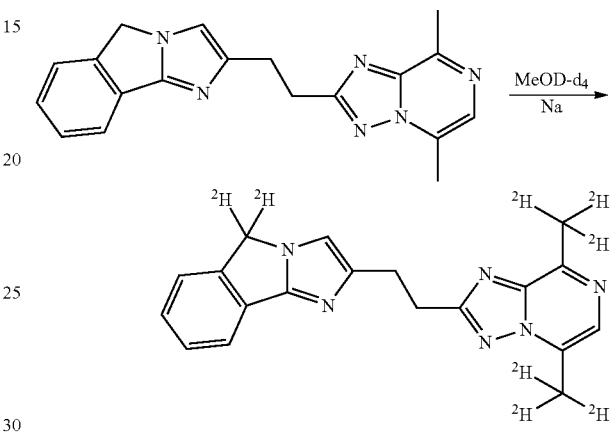

To a solution of sodium (30 mg, 1.3 mmol) dissolved in deutero-methanol (MeOD-d$_4$, 4 mL) was added 2-[-2-(5,8-Dimethyl-[1,2,4]-triazolo[1,5-a]pyrazin-2-yl)-ethyl]-5H-imidazo[2,1-a]isoindole (25 mg, 0.076 mmol) and the solution was stirred at RT for 48 h. The solvents were removed in vacuo and the residue dissolved in DCM (10 mL), washed with saturated sodium bicarbonate solution, brine and the organic layer separated. The organic layer was dried (MgSO4), filtered and the volatiles removed in vacuo to yield the title compound as an off white solid. (14 mg, 53%). $^1$H NMR (600 MHz, MeOD-d$_4$): δ 7.76 (s, 1H), 7.61 (d, J=7.5 Hz, 1H), 7.41 (d, J=7.5 Hz, 1H), 7.32 (t, J=7.5 Hz, 1H), 7.25 (t, J=7.5 Hz, 1H), 7.05 (s, 1H), 3.26 (dd, J=7.7 Hz, 2H), 3.13 (dd, J=7.7 Hz, 2H). LC-MS: m/z=338.4 (MH$^+$), t$_R$=0.71 minutes.

Pharmacological Testing

PDE10A Enzyme

Active PDE10A enzyme is prepared in a number of ways for use in PDE assays (Loughney, K. et al. *Gene* 1999, 234, 109-117; Fujishige, K. et al. *Eur J. Biochem.* 1999, 266, 1118-1127 and Soderling, S. et al. *Proc. Natl. Acad. Sci.* 1999, 96, 7071-7076). PDE10A can be expressed as full-length proteins or as truncated proteins, as long as they express the catalytic domain. PDE10A can be prepared in different cell types, for example insect cells or *E. coli*. An example of a method to obtain catalytically active PDE10A is as follows: The catalytic domain of human PDE10A (amino acids 440-779 from the sequence with accession number NP 006652) is amplified from total human brain total RNA by standard RT-PCR and is cloned into the BamH1 and Xho1 sites of the pET28a vector (Novagen). Expression in coli is performed according to standard protocols. Briefly, the expression plasmids are transformed into the BL21(DE3) *E. coli* strain, and 50 mL cultures inoculated with the cells allowed to grow to an OD600 of 0.4-0.6 before protein expression is induced with 0.5 mM IPTG. Following induction, the cells are incubated overnight at room temperature, after which the cells are collected by centrifugation. Cells expressing PDE10A are resuspended in 12 mL (50 mM TRIS-HCl-pH8.0, 1 mM MgCl$_2$ and protease inhibitors). The cells are lysed by sonication, and after all cells are lysed, TritonX100 is added according to Novagen protocols. PDE10A is partially purified on Q sepharose and the most active fractions were pooled.

PDE10A Inhibition Assay

A PDE10A assay may for example, be performed as follows: The assay is performed in 60 uL samples containing a fixed amount of the relevant PDE enzyme (sufficient to convert 20-25% of the cyclic nucleotide substrate), a buffer (50 mM HEPES7.6; 10 mM MgCl$_2$; 0.02% Tween20), 0.1 mg/ml BSA, 225 pCi of $^3$H-labelled cyclic nucleotide substrate, tritium labeled cAMP to a final concentration of 5 nM and varying amounts of inhibitors. Reactions are initiated by addition of the cyclic nucleotide substrate, and reactions are allowed to proceed for one hr at room temperature before being terminated through mixing with 15 uL 8 mg/mL yttrium silicate SPA beads (Amersham). The beads are allowed to settle for one hr in the dark before the plates are counted in a Wallac 1450 Microbeta counter. The measured signal can be converted to activity relative to an uninhibited control (100%) and IC$_{50}$ values can be calculated using the Xlfit extension to EXCEL.

In the context of the present invention the assay was performed in 60 uL assay buffer (50 mM HEPES pH 7.6; 10 mM MgCl$_2$; 0.02% Tween20) containing enough PDE10A to convert 20-25% of 10 nM $^3$H-cAMP and varying amounts of inhibitors. Following a 1 hour incubation the reactions were terminated by addition of 15 uL 8 mg/mL yttrium silicate SPA beads (Amersham). The beads were allowed to settle for one hr in the dark before the plates were counted in a Wallac 1450 Microbeta counter. IC$_{50}$ values were calculated by non linear regression using XLfit (IDBS).

Results of the experiments showed that the tested compounds of the invention inhibit the PDE10A enzyme with IC$_{50}$ values below 10 nM.

Phencyclidine (PCP) Induced Hyperactivity

Male mice (NMRI, Charles River) weighing 20-25 g are used. Eight mice are used in each group receiving the test compound (5 mg/kg) plus PCP (2.3 mg/kg) including the parallel control groups receiving the vehicle of the test compound plus PCP or vehicle injections only. The injection volume is 10 ml/kg. The experiment is made in normal light conditions in an undisturbed room. The test substance is injected per oss 60 min before injection of PCP, which is administered subcutaneous.

Immediately after injection of PCP the mice are placed individually in special designed test cage (20 cm×32 cm). The activity is measured by 5×8 infrared light sources and photocells spaced by 4 cm. The light beams cross the cage 1.8 cm above the bottom of the cage. Recording of a motility count requires interruption of adjacent light beams, thus avoiding counts induced by stationary movements of the mice.

Motility is recorded in 5 min intervals for a period of 1 hour. The drug effect is calculated on the total counts during the 1 hour behavioral test period in the following manner: The mean motility induced by vehicle treatment in the absence of PCP is used as baseline. The 100 percent effect of PCP is accordingly calculated to be total motility counts minus baseline. The response in groups receiving test compound is thus determined by the total motility counts minus baseline, expressed in percent of the similar result recorded in the parallel PCP control group. The percent responses are converted to percent inhibition.

Results of the experiments showed that the tested compound 2-[2-(5,8-dimethyl-[1,2,4]triazolo[1,5-a]pyrazin-2-yl)-ethyl]-5H-imidazo[2,1-a]isoindole is an in vivo active compound that inhibits the PCP induced hyperactivity
ED50=0.2 mg/kg;
Inhibition is 100% at 5 mg/kg.

The invention claimed is:

1. A compound having the structure I

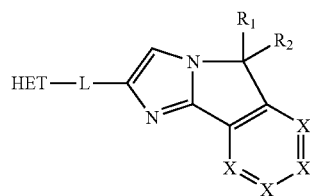

wherein

X is selected from the group consisting of CH, CF, COCH$_3$ and COH;'

R$_1$ and R$_2$ are each selected independently from the group consisting of H; C$_1$-C$_6$ alkyl; C$_1$-C$_6$ alkyl(C$_3$-C$_8$) cycloalkyl; C$_1$-C$_6$ hydroxyalkyl; C$_1$-C$_6$ alkoxy; CH$_2$CN; CH$_2$C(O)NH$_2$; C$_1$-C$_6$arylalkyl; C$_1$-C$_6$ alkyl-heterocycloalkyl; 4-chlorobenzyl; halogen; and hydroxy;

L is a linker selected from the group consisting of —CH$_2$—CH$_2$—, —CH=CH—, —CH$_2$—S—, and —S—CH$_2$—; and HET is a heteroaromatic group of formula II containing 2 to 4 nitrogen atoms:

wherein

Y is N or CH, Z is N or C; and

HET optionally is substituted with up to three substituents R$_5$, R$_6$ and R$_7$ individually selected from the group consisting of H; C$_1$-C$_6$ alkyl; halogen; cyano; halo(C$_1$-C$_6$) alkyl; aryl; C$_1$C$_6$ alkoxy, and C$_1$-C$_6$ hydroxyalkyl; wherein "*" denotes the attachment point;

or a pharmaceutically acceptable acid addition salt thereof.

2. The compound of claim 1 wherein HET is selected from the group consisting of [1,2,4]triazolo[1,5-a]pyrazine, [1,2,4]triazolo[1,5-a]pyridine, imidazo[1,2-a]pyridine, imidazo[4,5-b]pyrimidine;

pyrazolo [1,5-a]pyridine, [1,2,4]triazolo[1,5-a]pynmidine, [1,2,4]triazolo[1,5-c]pyrimidine, and imidazo [1,2-a]pyrimidine.

3. The compound of claim 1 wherein HET is selected from the group consisting of 5,8-dimethyl -[1,2,4]triazolo[1,5-a]pyrazine, 5,8-dimethyl-[1,2,4]triazolo[1,5-a]pyridine, 5-methyl-[1,2,4]triazolo[1,5-a]pyridine, and (5-methyl-[1,2,4]triazolo[1,5-a]pyrazin-8-yl)-methanol.

4. The compound of claim 1 wherein R$_5$, R$_6$ are independently selected from the group consisting of H, OH, fluoro, CH$_3$, and OCH$_3$.

5. The compound of claim 1 wherein $R_5$, $R_6$ and $R_7$ are independently selected from the group consisting of H, $CH_3$ and $OCH_3$.

6. The compound of claim 1, wherein $R_1$ and $R_2$ are independently selected from the group consisting of H, methyl, ethyl, 1-propyl, 2-propyl, isobutyl), cyclopropylmethyl, hydroxyethyl, methoxy, ethoxy, $CH_2CN$, $CH_2C(O)NH_2$, benzyl tetrahydropyran-4-yl-methyl, 2-morpholin-4-yl-ethyl, fluoro and hydroxy.

7. The compound of claim 1, wherein $R_5$,$R_6$,$R_7$ are independently selected from the group consisting of H, methyl, chloro, fluoro, bromo, cyano, trifluoromethyl, phenyl, methoxy, ethoxy, and $CH_2CH_2OH$.

8. The compound of claim 1, wherein the compound is selected from the group consisting of
- 2-[2-(5,8-dimethyl-[1,2,4]triazolo[1,5-a]pyrazin-2-yl)-ethyl]-5H-imidazo[2,1-a]isoindole;
- 2-[2-(5,8-dimethyl-[1,2,4]triazolo[1,5-a]pyridin-2-yl)-ethyl]-5H-imidazo[2,1-a]isoindole;
- 2-[2-(5,8-methyl-[1,2,4]triazolo[1,5-a]pyridin-2-yl)-ethyl]-5H-imidazo[2,1-a]isoindole;
- 2-[2-(5,8-dimethyl-[1,2,4]triazolo[1,5-a]pyrazin -2-yl)-vinyl]-5H-imidazo[2,1-a]isoindole;
- {2-[2-(5H-imidazo-[2,1-a]isoindol-2-yl)-ethyl]-5-methyl-[1,2,4]triazolo[1,5-a]pyrazin-8-yl}-methanol; and
- 2-[2-(5,8-dimethyl-[1,2,4]triazolo[1,5-a]pyrazin-2-yl)-ethyl]-7-fluoro-5H-imidazo[2,1-a]isoindole; or a pharmaceutically acceptable acid addition salt thereof.

9. The compound of claim 8, wherein the compound is 2-[2-(5,8-dimethyl-[1,2,4]triazolo[1,5-a]pyrazin-2-yl)-ethyl]-5H-imidazo[2,1-a]isoindole.

10. The compound of claim 8, wherein the compound is 2-[2-(5,8-dimethyl[1,2,4]triazolo[1,5-a]pyridin-2-yl)-ethyl]-5H-imidazo[2,1-a]isoindole.

11. The compound of claim 8, wherein the compound is 2-[2-(5-methyl-[1,2,4]triazolo[1,5-a]pyridin-2-yl)-ethyl]-5H-imidazo[2,1-a]isoindole.

12. The compound of claim 8, wherein the compound is 2-[2-(5,8-dimethyl-[1,2,4triazolo1,5-a]pyrazin-2-yl)-vinyl]-5H-imidazo [2,1-a]isoindole.

13. The compound of claim 8, wherein the compound is {2-[2-(5H-imidazo[2,1-a]isoindol-2-yl)-ethyl]-5-methyl-[1,2,4triazolo[1,5-a ]pyrazin-8-yl}-methanol.

14. The compound of claim 8, wherein the compound is 2-2-(5,8-dimethyl-[1,2,4]triazolo[1,5-a]pyrazin-2-yl)-ethyl]-7-fluoro-5H-imidazo[2,1-a]isoindole.

15. A pharmaceutical composition comprising a therapeutically effective amount of the compound of claim 1 and a pharmaceutically acceptable carrier, excipient or diluent.

* * * * *

UNITED STATES PATENT AND TRADEMARK OFFICE
CERTIFICATE OF CORRECTION

PATENT NO.        : 8,552,045 B2
APPLICATION NO.   : 13/299368
DATED             : October 8, 2013
INVENTOR(S)       : Jan Kehler et al.

It is certified that error appears in the above-identified patent and that said Letters Patent is hereby corrected as shown below:

In the Claims:

Please amend claim 8, at column 33, line 20, to recite "2-[2-(5-methyl-[1,2,4]triazolo[1,5-a]pyridin-2-yl)-ethyl]-5H-imidazo[2,1-a]isoindole;" in lieu of "2-[2-(5,8-methyl-[1,2,4]triazolo[1,5-a]pyridin-2-yl)-ethyl]-5H-imidazo[2,1-a]isoindole;"

Signed and Sealed this
Fourteenth Day of July, 2015

Michelle K. Lee
*Director of the United States Patent and Trademark Office*